(12) United States Patent
Sharma et al.

(10) Patent No.: US 7,425,608 B2
(45) Date of Patent: Sep. 16, 2008

(54) METHOD OF MAKING METALLOPEPTIDES

(75) Inventors: Shubh D. Sharma, Cranbury, NJ (US); Yi-Qun Shi, East Brunswick, NJ (US)

(73) Assignee: Palatin Technologies, Inc., Cranbury, NJ (US)

( * ) Notice: Subject to any disclaimer, the term of this patent is extended or adjusted under 35 U.S.C. 154(b) by 61 days.

(21) Appl. No.: 11/221,210

(22) Filed: Sep. 7, 2005

(65) Prior Publication Data

US 2006/0003386 A1 Jan. 5, 2006

Related U.S. Application Data

(62) Division of application No. 09/883,069, filed as application No. PCT/US99/29743 on Dec. 14, 1999, now abandoned.

(60) Provisional application No. 60/112,235, filed on Dec. 14, 1998.

(51) Int. Cl.
*C07K 7/00* (2006.01)
*C12Q 1/38* (2006.01)

(52) U.S. Cl. ............... 530/336; 530/335; 530/334; 530/333; 530/326; 530/327; 530/328; 530/329; 530/330; 530/331

(58) Field of Classification Search ........... 530/336, 530/326–335
See application file for complete search history.

(56) References Cited

U.S. PATENT DOCUMENTS

| 5,668,254 A | | 9/1997 | Deghenghi |
| 5,770,178 A | | 6/1998 | Itaya et al. |
| 5,891,418 A | * | 4/1999 | Sharma ............... 424/1.69 |
| 5,976,495 A | * | 11/1999 | Pollak et al. ......... 424/1.69 |
| 5,980,861 A | | 11/1999 | Hnatowich et al. |
| 6,027,711 A | | 2/2000 | Sharma |
| 6,048,527 A | | 4/2000 | Granoff et al. |
| 7,045,503 B1 | * | 5/2006 | McBride et al. ............. 514/6 |
| 2001/0009899 A1 | | 7/2001 | Keri et al. |
| 2002/0012948 A1 | | 1/2002 | Sharma et al. |

OTHER PUBLICATIONS

Fabris, D., et al., "Investigation of Zinc Chelation in Zinc-Finger Arrays by Electrospray Mass Spectrometry", *Inorganic Chemistry*, vol. 38, (1999), 1322-1325.

Giblin, Michael F., et al., "Design and Characterization of ()-melanocortin Peptide Analogs Cyclized through Rhenium and Technetium Metal Coordination", *Proceedings of National Academy Science USA*, Vo.. 95 (Oct. 1998), 12814-12818.

Shi, Yi-Qun, et al., "Conformationally Constrained Metallpeptide Template for Melanocortin-1 Receptor", *American Chemical Society, 218th ACS National Meeting, Abstracts of Papers, Part 1, Abstract MEDI 257,U* (Aug. 22, 1999).

Guibe, Francois; "Allylic Protecting Groups and Their Use in a Complex Environment", *Tetrahedron 54, Report No. 444*, (1998) 2967-3042.

* cited by examiner

*Primary Examiner*—T. D. Wessendorf
(74) *Attorney, Agent, or Firm*—Stephen A. Slusher

(57) ABSTRACT

Method of making metallopeptides is provided, for use in biological, pharmaceutical and related applications. The metallopeptides are made of peptides, peptidomimetics and peptide-like constructs, and include a metal ion-binding region thereof which includes at least one orthogonal sulfur-protecting group, in which the peptide, peptidomimetic or construct is conformationally fixed on deprotection of the sulfur and complexation of the metal ion-binding region with a metal ion while the peptide, peptidomimetic or construct is cleavably bound to solid phase.

4 Claims, 6 Drawing Sheets

A

B

C

D

E

F

G

H

I

J

METHOD OF MAKING METALLOPEPTIDES

CROSS-REFERENCE TO RELATED APPLICATIONS

This application is a divisional application of U.S. patent application 09/883,069, entitled Metallopeptide Combinatorial Libraries and Applications, filed on Jun. 14, 2001, now abandoned, which was a national stage application of International Application PCT/US99/29743, entitled Metallopeptide Combinatorial Libraries and Applications, filed on Dec. 14, 1999, which claimed the benefit of the filing of U.S. Provisional Patent Application Ser. No. 60/112,235, entitled Metallopeptide Combinatorial Libraries and Application, filed on Dec. 14, 1998, and the specifications thereof of each is incorporated herein by reference.

BACKGROUND OF THE INVENTION

1. Field of the Invention (Technical Field)

The present invention relates to solid and solution phase metallopeptide combinatorial libraries, metal ion-complexed peptidomimetic and peptide-like combinatorial libraries and metallo-construct combinatorial libraries, wherein at least a portion of each library constituent is conformationally constrained upon complexation with a metal ion, and methods for use and making of the same. The invention also relates to methods for synthesizing and assembling such libraries, and methods for identification and characterization of library constituents which are capable of binding a target molecule of interest, or mediating a biological activity of interest.

2. Background Art

Peptide Libraries and Combinatorial Chemistry. U.S. patent application Ser. No. 08/660,697 (the "'697 application") teaches general combinatorial chemistry techniques for metallopeptides, including prior art methods now well recognized tools for rapid drug discovery. A library of peptides and other small molecules, with its enormous pool of structurally diverse molecules, is well suited for both lead generation as well as lead optimization. Libraries of a variety of molecular species have been described in literature and screened for drug discovery, including peptides, peptoids, peptidomimetics, oligonucleotides, benzodiazepines, and other libraries of small organic molecules.

Various approaches have been used to construct libraries of structurally diverse chemical compounds, include chemical synthesis and genetic engineering methods. Chemically synthesized libraries have been synthesized by general solution chemical means and by solid-phase methods. The prior art on designing, synthesizing, screening, and evaluation of peptide-based libraries has been reviewed in numerous articles, including the following, incorporated herein by reference: Pinilla C et al, *Biopolymers (Peptide Sci)* 37:221-240, 1995; Lebl M et al, *Biopolymers (Peptide Sci)* 37:177-198, 1995; Lam K S et al, *Chemical Reviews* 97:411-448, 1997; Smith G P and Petrenko G P, *Chemical Reviews* 97:391-410, 1997; Nefzi A et al, *Chemical Reviews* 97:449-472, 1997; Holmes C P et al, *Biopolymers (Peptide Sci)* 37:199-211, 1995; and, Moran E J et al, *Biopolymers (Peptide Sci)* 37:213-219, 1995.

Spatially Addressable Parallel Synthesis of Solid Phase Bound Libraries. Various strategies for chemical construction of a library of peptides or other small molecules are also well established. One strategy involves spatially separate synthesis of compounds in parallel on solid phase or on a solid surface in a predetermined fashion so that the location of one compound or a subset of compounds on the solid surface is known. The first such method was developed by Geysen for peptide epitope mapping (Geysen H M, Meloen R H, Bartel- ing S J: *Proc Natl Acad Sci USA* 81:3998-4002, 1984). This method involves synthesis of various sets and subsets of a library of peptides on a multiple number of polypropylene pin tips in a predetermined fashion. The assembly of a library of greater than 10,000 molecules by this method is, however, cumbersome and time consuming. The light-directed spatially addressable parallel chemical synthesis technique (Fodor S P A et al: *Science* 251:767-773, 1991), based upon use of photolithographic techniques in peptide synthesis on a solid surface, such as a borosilicate glass microscope slide, is a better method of constructing libraries containing more than 100,000 spatially separated compounds in a pre-determined fashion. However, synthesis of libraries that are structurally more diverse than simple peptides requires the development of orthogonal photolabile protecting groups that can be cleaved at different wavelengths of light. In addition, the solid surface bearing these libraries also has been reported to cause a pronounced effect on binding affinities in library screening assays (Cho C Y et al: *Science* 261:1303-1305, 1993; Holmes C P et al: *Biopolymers* 37:199-211, 1995).

The DIVERSOMER® apparatus designed by DeWitt and coworkers at Parke-Davis Pharmaceutical Research Division of Warner-Lambert Company, Ann Arbor, Mich., USA, offers a convenient and automated method of parallel synthesis of small organic molecule libraries on a solid phase (DeWitt S H et al: *Proc Natl Acad Sci USA* 90:6909-6913, 1993; U.S. Pat. No. 5,324,483; DeWitt S H et al: *Acc Chem Res* 29:114-122, 1996). Another conceptually similar apparatus for the solid phase synthesis of small organic molecule libraries has been reported by Meyers and coworkers (Meyers H V et al: *Molecular Diversity* 1: 13-20, 1995).

Pooling and Split Synthesis Strategies. Large libraries of compounds can be assembled by a pooling strategy that employs equimolar mixtures of reactants in each synthetic step (Geysen H M et al: *Mol Immunol* 23:709-715, 1986) or preferably by adjusting the relative concentration of various reactants in the mixture according to their reactivities in each of the coupling reactions (Ostresh J M et al: *Biopolymers* 34:1681-1689, 1994; U.S. Pat. No. 5,010,175 to Rytter W J and Santi D V). In one approach equimolar mixtures of compounds are obtained by splitting the resin in equal portions, each of which is separately reacted with each of the various monomeric reagents. The resin is mixed, processed for the next coupling, and again split into equal portions for separate reaction with individual reagents. The process is repeated as required to obtain a library of desired oligomeric length and size. This approach is also the basis of the "one-bead one-peptide" strategy of Furka et al. and Lam et al. (Furka et al: *Int. J. Peptide Protein Res.* 37:487, 1991; Lam K S et al: *Nature* 354:82-84, 1991; Lam K S et al: *Nature* 360:768, 1992) which employs amino acid sequencing to ascertain the primary structure of the peptide on a hit bead in a bioassay. Automated systems have been developed for carrying out split synthesis of these libraries with rather more efficiency (Zukermann R N et al: *Peptide Res* 5:169-174, 1992; Zukermann R N et al: *Int J Peptide Protein Res* 40:497-506, 1992). A common artifact occasionally seen with all these resin bound libraries is altered target-specific affinity by some solid phase bound compounds in bioassays, which can result in totally misleading results.

Another strategy involves construction of soluble libraries (Houghten R A et al: *Proc Natl Acad Sci USA* 82:5131-5135, 1985; Berg et al: *J Am Chem Soc* 111:8024-8026, 1989; Dooley C T et al: *Science* 266:2019-2022, 1994; Blondelle S E: *Antimicrob Agents Chemother* 38:2280-2286, 1994; Panilla C: *Biopolymers* 37:221-240, 1995). This strategy involves a deconvolution process of iterative re-synthesis and bioassaying until all the initially randomized amino acid positions are defined. Several modifications to this strategy have been developed, including co-synthesis of two libraries containing orthogonal pools, as demonstrated by Tartar and coworkers, which eliminates the need of iterative re-synthesis and evaluation (Deprez B et al: *J Am Chem Soc* 117: 5405-5406, 1995). The positional scanning method devised by Houghton and coworkers eliminates iterative re-synthesis (Dooley C T et al: *Life Sci* 52:1509-1517, 1993; Pinilla C et al: *Biotechniques* 13:901-905, 1992; Pinilla C et al: *Drug Dev Res* 33:133-145, 1992). A combination of this strategy with the split synthesis methods described above has also been described (Erb E et al: *Proc Natl Acad Sci USA*, 91:11422-11426, 1994). A major limitation of the soluble library approach is its applicability to high affinity systems. The abundance of each compound in solution can be influenced by the total number of compounds in a library which can affect the biological activity. For this reason, a highly active compound in any pool may not in fact be the most potent molecule. Lack of reasonable solubilities of certain members in a library may further influence this phenomenon. In fact, for several libraries the most active peptide was not even identified in the most active library pool (Dooley C T et al: *Life Sci* 52:1509-1517, 1993; Eichler J, in *Proc . 23rd Eur. Peptide Symp.*, Berga, September 1994, Poster 198; Wyatt J R: *Proc Natl Acad Sci USA*, 91:1356-1360, 1994).

Various strategies for determination of the structure for a positive hit in a random library have been developed. See, e.g., U.S. Pat. No. 5,698,301. For a solid-phase library, direct analytical modalities include Edman degradation for peptide libraries, DNA sequencing of oligonucleotide libraries, and various mass spectrometry techniques on matrix bound compounds. The technique of creating a series of partially end-capped compounds at each of the synthetic steps during library assembly helps their unambiguous identification by mass spectrometry (Youngquist R S et al: *J Am Chem Soc* 117:3900-3906, 1995; Youngquist R S et al: *Rapid Commun Mass Spectr* 8:77-81, 1994). Direct mass spectrometric analysis of compounds covalently bound to a solid phase matrix of particles is also now possible by the use of matrix-assisted laser desorption/ionization (MALDI) techniques (Siuzdak G et al: *Bioorg Med Chem Lett* 6:979, 1996; Brown B B et al: *Molecular Diversity* 1:4-12, 1995). In addition to these analytical techniques, various encoding strategies have been devised for structure elucidation in organic molecule-based libraries, including both non-peptide and non-nucleotide libraries, such as DNA encoding, peptide coding, haloaromatic tag encoding, and encoding based on radiofrequency transponders. See, e.g., U.S. Pat. No. 5,747,334.

Most of the libraries described above are termed "random" libraries because of their enormous structural and conformational diversity. Libraries of relatively restricted and biased structures have also been reported. Examples of libraries of conformationally rigid compounds built on a structurally common template include benzodiazepine, β-lactam, β-turn mimetics, diketopiperazines, isoquinolines, dihydro- and tetrahydroisoquinolines, 1,4 dihydropyridines, hydantoins, pyrrolidines, thiazolidine-4-carboxylic acids, 4-thiazolidines and related 4-metathiazanones and imidazoles.

Among the various classes of libraries of small molecules, peptide libraries remain the most versatile because of the structural diversity offered by the use of naturally occurring amino acids, incorporation of a variety of "designer" amino acids, and the high efficiency and ease with which peptide synthesis can be accomplished. In addition, another level of structural diversity in peptide-based libraries has been added by post-synthesis modification of the libraries. These modifications include permethylation, acylation, functionalization of the side chain functionality, and reductive amination of the N-terminus.

Many libraries specifically customized for one particular biological target have also been reported. These libraries are generally assembled by incorporating only a set of structural elements that might be essential for eliciting a target-specific response. Some of the reported libraries of this class include aspartic acid protease, zinc proteases, carbonic anhydrase inhibitors, tyrosine kinase inhibitors, estrogen receptor ligands, and antioxidants.

SUMMARY OF THE INVENTION (DISCLOSURE OF THE INVENTION)

The present invention provides a combinatorial library of different sequence peptide members synthesized on solid phase, where each constituent library member includes a) a peptide sequence of three or more amino acid residues bound to solid phase characterized by (i) a sequence of two or more amino acid residues forming a metal ion-binding domain and including at least one amino acid residue containing at least one S wherein the said S is protected by an orthogonal S-protecting group, (ii) a sequence of one or more amino acid residues at the N- or C-terminus of the metal ion-binding domain, or at both the N- and C-terminus of the metal ion-binding domain, and (iii) a cleavable bond attaching the peptide sequence to solid phase; and (b) a unique selection or sequence of amino acid residues in the peptide sequence of at least one of the constituent members of the library. In this library, the orthogonal S-protecting group may be removed without cleaving the peptide sequence from the solid phase.

The invention further provides a combinatorial library of different sequence peptidomimetic members synthesized on solid phase, where each constituent library member includes (a) a peptidomimetic sequence of a combination of three or more amino acid residues and mimics of amino acid residues bound to solid phase characterized by (i) a sequence of two or more amino acid residues, mimics of amino acid residues or combinations thereof forming a metal ion-binding domain and including at least one amino acid residue or mimic of an amino acid residue containing at least one S wherein the said S is protected by an orthogonal S-protecting group, (ii) a sequence of one or more amino acid residues, mimics of amino acid residues or combinations thereof at the N- or C-terminus of the metal ion-binding domain, or at both the N- and C-terminus of the metal ion-binding domain, and (iii) a cleavable bond attaching the peptidomimetic sequence to solid phase; and (b) a unique selection or sequence of amino acid residues, mimics of amino acid residues or combinations thereof in the peptidomimetic sequence of at least one of the constituent members of the library. In this library, the orthogonal S-protecting group may be removed without cleaving the peptidomimetic sequence from the solid phase.

The invention further provides a combinatorial library of different sequence peptide or peptidomimetic members synthesized in solution, where each constituent library member includes (a) a peptidomimetic sequence of a combination of three or more amino acid residues and mimics of amino acid residues characterized by (i) a sequence of two or more amino acid residues, mimics of amino acid residues or combinations thereof forming a metal ion-binding domain and including at least one amino acid residue or mimic of an amino acid residue containing at least one S wherein the said S is protected by an orthogonal S-protecting group, (ii) a sequence of one or more amino acid residues, mimics of amino acid residues or combinations thereof at the N- or C-terminus of the metal ion-binding domain, or at both the N- and C-terminus of the metal ion-binding domain; and (b) a unique selection or sequence of amino acid residues, mimics of amino acid residues or combinations thereof in the peptidomimetic sequence of at least one of the constituent members of the library. In this library and the other libraries provided above, the members may include a sequence with at least one amino acid residue or mimic of an amino acid residue containing at least one sulfur atom in which the sulfur atom is protected by a non-orthogonal S-protecting group. In this library and the other libraries provided above, the orthogonal S-protecting group may be removed without removing the non-orthogonal S-protecting group.

In any of the foregoing combinatorial libraries, the metal ion-binding domain can further include at least one N available for binding to a metal ion upon removal of the orthogonal S-protecting group. In one embodiment, the metal ion-binding domain consists of three residues forming an $N_3S_1$ ligand. The orthogonal S-protecting group may be S-thio-butyl, acetamidomethyl, 4-methoxytrityl, S-sulfonate or 3-nitro-2-pyridinesulfenyl, and the orthogonal S-protecting group may further be removed without otherwise altering the constituent library member. Structural diversity may occur in the metal ion-binding domain, or the residues and sequence of residues comprising the metal ion-binding domain can be fixed, with structural diversity occurring elsewhere in the sequence.

In the case of peptide libraries, the amino acid residue containing at least one S protected by an orthogonal S-protecting group can be an L- or D-3-mercapto amino acid, including but not limited to L- or D-cysteine or L- or D-penicillamine. In the combinatorial libraries that include peptidomimetic members, the amino acid residue or mimic of an amino acid residue containing at least one S protected by an orthogonal S-protecting group can be an L- or D-3-mercapto amino acid, including but not limited to L- or D-cysteine or L- or D-penicillamine; 3-mercapto phenylananine; 2-mercaptoacetic acid; 3-mercaptopropionic acid; 2-mercaptopropionic acid; 3-mercapto-3,3,-dimethyl propionic acid; 3-mercapto-3,3,-diethyl proprionic acid; 3-mercapto,3-methyl propionic acid; 2-mercapto,2-methyl acetic acid; 3-cyclopentamethlene,3-mercaptopropionic acid; or 2-cyclopentamethlene, 2-mercaptoacetic acid.

The invention further includes a method for generating a metallopeptide or metallopeptidomimetic combinatorial library, including the steps of (a) constructing a library containing a plurality of sequences of the formula Aaa-MBD-Baa cleavably bound to solid phase, wherein (i) MBD includes at least two amino acid residues, mimics of amino acid residues or combinations thereof, with at least one of said residues comprising at least one nitrogen atom available to complex with the coordination sphere of a metal ion, the metal ion to be provided, and with at least one of said residues comprising at least one sulfur atom protected by an orthogonal S-protecting group; (ii) Aaa and Baa each include from 0 to about 20 amino acid residues, mimics of amino acid residues or combinations thereof, provided that the combination of Aaa and Baa contain at least 1 amino acid residue or mimic of an amino acid residue, and provided that between at least two of the plurality of sequences of the formula Aaa-MBD-Baa at least either Aaa or Baa differ in at least either the sequence of residues or the selection of residues; (b) deprotecting the sulfur atom protected by an orthogonal S-protecting group by cleaving the orthogonal S-protecting group without cleaving the sequence from the solid phase; and (c) complexing a metal ion to the MBD. The resulting metal ion-complexed sequences form a metallopeptide or metallopeptidomimetic combinatorial library. The method can optionally include the step (d) of cleaving the sequence from the solid phase.

The invention further includes a method for producing substantially pure metallopeptides or metallopeptidomimetics without a solution purification step, including the steps of: (a) synthesizing a sequence of the formula Aaa-MBD-Baa cleavably bound to solid phase, wherein (i) MBD includes at least two amino acid residues, mimics of amino acid residues or combinations thereof, with at least one residues including at least one nitrogen atom available to complex with the coordination sphere of a metal ion, the metal ion to be provided, and with at least one residue including at least one sulfur atom protected by an orthogonal S-protecting group; (ii) Aaa and Baa each contain from 0 to about 20 amino acid residues, mimics of amino acid residues or combinations thereof; (b) deprotecting the sulfur atom protected by an orthogonal S-protecting group by cleaving the orthogonal S-protecting group without cleaving the sequence from the solid phase; (c) complexing a metal ion to the MBD; (d) cleaving the metal ion-complexed sequence from the solid phase; and (e) recovering the resulting substantially pure metal ion-complexed sequence.

In either of the foregoing methods, the step of deprotecting the sulfur atom protected by an orthogonal S-protecting group can be performed concurrent with the step of complexing a metal ion to the MBD. It is also possible and contemplated that the step of deprotecting the sulfur atom protected by an orthogonal S-protecting group can be performed prior to the step of complexing a metal ion to the MBD. In both methods, the step of deprotecting the sulfur atom protected by an orthogonal S-protecting group can be performed without cleaving any other amino acid side chain protecting group. In both methods, the residue including a sulfur atom protected by an orthogonal S-protecting group can be an L- or D-3-mercapto amino acid, including but not limited to L- or D-cysteine or L- or D-penicillamine; 3-mercapto phenylananine; 2-mercaptoacetic acid; 3-mercaptopropionic acid; 2-mercaptopropionic acid; 3-mercapto-3,3,-dimethyl propionic acid; 3-mercapto,3-methyl propionic acid; 3-mercapto-3,3,-diethyl proprionic acid; 2-mercapto,2-methyl acetic acid; 3-cyclopentamethlene,3-mercaptop acid; or 2-cyclopentamethlene,2-mercaptoacetic acid. In the methods, the MBD can be three residues forming an $N_3S_1$ ligand. The orthogonal S-protecting group can be S-thio-butyl, acetamidomethyl, 4-methoxytrityl, S-sulfonate or 3-nitro-2-pyridinesulfenyl. Any metal ion may be employed, including V, Mn, Fe, Co, Ni, Cu, Zn, Ga, As, Se, Y, Mo, Tc, Ru, Rh, Pd, Ag, Cd, In, Sn, W, Re, Os, Ir, Pt, Au, Hg, TI, Pb, Bi, Po, At, Sm, Eu and Gd.

In each of the methods and libraries provided, a specific conformational restriction is obtained upon complexing the peptides or amino acid sequences with a metal ion, such that the conformationally constrained peptide-metal ion complexes can serve as surrogates for reverse turn structures, such as beta turns and gamma turns commonly found in naturally occurring peptides and proteins.

Accordingly, it is an object of this invention to provide libraries of conformationally constrained peptide-metal ion complexes as surrogates for reverse turn structures, such as beta turns and gamma turns commonly found in naturally occurring peptides and proteins. The turns formed as a consequence of metal ion complexation are more stable than the naturally occurring turn structures, which are stabilized only by weaker interactions such as van der Waals, interactions and hydrogen bonds.

Another object of this invention is to provide combinatorial peptide libraries of peptide-metal ion complexes, wherein the peptides include a metal ion-binding domain, such that a specific conformational structure is obtained upon metal complexation.

Another object of this invention to provide combinatorial peptide libraries of peptide-metal ion complexes, wherein the amino acids comprising the peptides may be naturally occurring amino acids, isomers and modifications of such amino acids, non-protein amino acids, post-translationally modified amino acids, enzymatically modified amino acids, constructs or structures designed to mimic amino acids, and the like, so that the library includes pseudopeptides and peptidomimetics.

Another object of this invention is to provide metallopeptide libraries, wherein the metallopeptides include a metal ion-binding domain, such that a specific conformational structure is obtained upon metal complexation, and the metallopeptides further include distinct, unique and different amino acid sequences.

Another object of this invention is to provide metallopeptide libraries, wherein the metallopeptides include a metal ion-binding domain and distinct, unique and different amino acid sequences, wherein the metallopeptides may be exposed to a substance to which one or more metallopeptides will exhibit specificity and affinity for the substance of interest.

Another object of this invention is to provide metallopeptide libraries, wherein the metallopeptides include a metal ion-binding domain and distinct, unique and different amino acid sequences, wherein the metallopeptides may be exposed to a substance to which one or more determinable metallopeptides will preferentially bind.

Another object of this invention is to provide metallopeptide libraries, wherein the metallopeptides include a metal ion-binding domain, which may be either soluble or solid phase libraries.

Another object of this invention is to provide methods for synthesis of peptides wherein the peptides contain one or more reactive SH groups forming a part of a metal ion-binding domain, whereby the reactive SH groups are protected during synthesis, and are deprotected only upon complexing the peptides with a metal ion. For solid phase libraries, such deprotection, and subsequent metal ion complexation occurs in solid phase, with the peptides being optionally subsequently cleaved from solid phase.

Another object of this invention is to provide combinatorial metallopeptide libraries wherein each of the peptides forming the library contain a reverse turn structure as a consequence of metal ion complexation.

Another object of this invention is to provide combinatorial metallopeptide libraries containing metallopeptides with high specificity and affinity for the target molecule of interest, such high specificity and affinity resulting from each of the peptides forming the library containing a reverse turn structure as a consequence of metal ion complexation.

Another object of this invention is to provide a method for rapid and efficient complexation of a pool of diverse peptides with a metal ion, including a rhenium metal ion.

Another object of this invention is to provide a method for the identification of specific metallopeptides through internal signatures resulting from use of metal ions with two or more isotopic peaks, such as through use of rhenium containing two isotopes in fixed relative abundance that differ in mass by 2 units.

Other objects, advantages and novel features, and the further scope of applicability of the present invention, will be set forth in part in the detailed description to follow, taken in conjunction with the accompanying drawings, and in part will become apparent to those skilled in the art upon examination of the following, or may be learned by practice of this invention. The objects and advantages of this invention may be realized and attained by means of the instrumentalities and combinations particularly pointed out in the appended claims.

BRIEF DESCRIPTION OF THE DRAWINGS

The accompanying drawings, which are incorporated into and form a part of the specification, illustrate several embodiments of the present invention and, together with the description, serve to explain the principles of the invention. The drawings are only for the purpose of illustrating a preferred embodiment of the invention and are not to be construed as limiting the invention. In the drawings.

DESCRIPTION OF THE PREFERRED EMBODIMENTS

BEST MODES FOR CARRYING OUT THE INVENTION

Figure 1A:
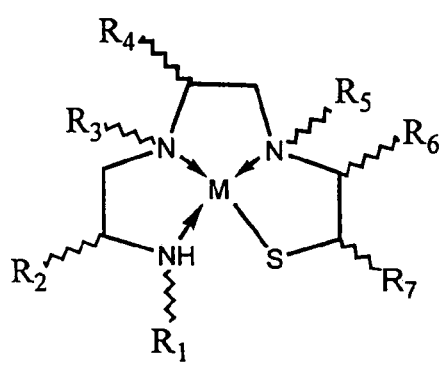
FIGS. 1A-1J Examples of molecular templates which may be employed in the libraries and structures of this invention. $R_1$ through $R_7$ are variable functional groups which may be employed to obtain the desired specificity, affinity and potency for a target molecule upon complexation of the metal ion, and M is a metal ion, or a metal-oxo (M=O) group, or a metal-nitrido (M/N) group, or a nitrido-N-substituted metal-nitrido (M=N—$R_8$) group where $R_8$ is a functional group which may contribute to the desired specificity and affinity for the target molecule, and where M is further employed to fix the structure in a specific conformational restriction upon complexation of the metal ion.

Definitions. Certain terms as used throughout the specification and claims are defined as follows:

The terms "bind," "binding," "complex," and "complexing," as used throughout the specification and claims, are generally intended to cover all types of physical and chemical binding, reactions, complexing, attraction, chelating and the like.

The "peptides" of this invention can be a) naturally-occurring, b) produced by chemical synthesis, c) produced by recombinant DNA technology, d) produced by biochemical or enzymatic fragmentation of larger molecules, e) produced by methods resulting from a combination of methods a through d listed above, or f) produced by any other means for producing peptides.

By employing chemical synthesis, a preferred means of production, it is possible to introduce various amino acids which do not naturally occur along the chain, modify the N- or C-terminus, and the like, thereby providing for improved stability and formulation, resistance to protease degradation, and the like.

The term "peptide" as used throughout the specification and claims is intended to include any structure comprised of two or more amino acids, including chemical modifications and derivatives of amino acids. For the most part, the peptides of this invention comprise fewer than 100 amino acids, and preferably fewer than 60 amino acids, and most preferably ranging from about 2 to 20 amino acids. The amino acids forming all or a part of a peptide may be naturally occurring amino acids, stereoisomers and modifications of such amino acids, non-protein amino acids, post-translationally modified amino acids, enzymatically modified amino acids, constructs or structures designed to mimic amino acids, and the like, so that the term "peptide" includes pseudopeptides and peptidomimetics, including structures which have a non-peptidic backbone. The term "peptide" also includes dimers or multimers of peptides. A "manufactured" peptide includes a peptide produced by chemical synthesis, recombinant DNA technology, biochemical or enzymatic fragmentation of larger molecules, combinations of the foregoing or, in general, made by any other method.

The "amino acids" used in this invention, and the term as used in the specification and claims, include the known naturally occurring protein amino acids, which are referred to by both their common three letter abbreviation and single letter abbreviation. See generally *Synthetic Peptides: A User's Guide*, G A Grant, editor, W.H. Freeman & Co., New York, 1992, the teachings of which are incorporated herein by reference, including the text and table set forth at pages 11 through 24. As set forth above, the term "amino acid" also includes stereoisomers and modifications of naturally occurring protein amino acids, non-protein amino acids, post-translationally modified amino acids, enzymatically synthesized amino acids, derivatized amino acids, constructs or structures designed to mimic amino acids, and the like. Modified and unusual amino acids are described generally in *Synthetic Peptides: A User's Guide*, cited above; Hruby V J, Al-obeidi F and Kazmierski W: *Biochem J* 268:249-262, 1990; and Toniolo C: *Int J Peptide Protein Res* 35:287-300, 1990; the teachings of all of which are incorporated herein by reference. A single amino acid is sometimes referred to herein as a "residue."

The library constructs of this invention also include a metal ion, which may be an ionic form of any element in metallic form, including but not limited to metals and metalloids. The metal ion may, but need not, be radioactive, paramagnetic or superparamagnetic. The metal ion can be of any oxidation state of any metal, including oxidation states of vanadium (V), manganese (Mn), iron (Fe), cobalt (Co), nickel (Ni), copper (Cu), zinc (Zn), gallium (Ga), arsenic (As), selenium (Se), yttrium (Y), molybdenum (Mo), technetium (Tc), ruthenium (Ru), rhodium (Rh), palladium (Pd), silver (Ag), cadmium (Cd), indium (In), tin (Sn), tungsten (W), rhenium (Re), osmium (Os), iridium (Ir), platinum (Pt), gold (Au), mercury (Hg), thallium (Tl), lead (Pb), bismuth (Bi), polonium (Po), astatine (At), samarium (Sm), europium (Eu), and gadolinium (Gd). The metal ion can also be a radionuclide of any of the foregoing, including In, Au, Ag, Hg, Tc, Re, Sn, At, Y and Cu. A preferred metal ion with a tetradentate coordination sphere is Re. For radiopharmaceutical applications, or applications wherein a radioisotope is desirable for screening, an alpha-, gamma- or beta-emitting radionuclide may be employed.

The coordination sphere of various common metal ions, in general, is tetradentate to hexadentate. In one embodiment according to this invention, an amino acid or amino acid mimetic sequence is included within each library member such that it contains the desired number of groups (4 to 6 in most cases) for complexing with the metal. The molecule is designed so that, upon complexing with a metal, it forms a mimic of a reverse turn structure about the site of metal complexation. A metal with coordination number 4, 5 or 6, and complexing respectively with an amino acid sequence forming a tetra, penta, or hexadentate ligand, will fold and constrain the ligand. The amino acid or amino acid mimetic sequence forming a ligand is defined as the metal ion-binding domain ("MBD") of the peptide or peptidomimetic. A highly flexible molecule like a peptide, in other words, is folded to form a kind of reverse turn upon its complexation with a metal. This resulting turn is a highly constrained structure in the conformational sense.

The biological-binding domain ("BBD") of the peptide or peptidomimetic is defined in the specification and claims as a sequence of one or more amino acids which constitute a biologically active sequence, exhibiting binding to a biological receptor found on cells, tissues, organs and other biological materials, thereby constituting the peptide as a member of a specific binding pair. The BBD also includes any sequence, which may be consecutive amino acids or mimetics (sychnological) or non-consecutive amino acids or mimetics (rhegnylogical) which forms a ligand, which ligand is capable of forming a specific interaction with its acceptor or receptor. The term "receptor" is intended to include both acceptors and receptors. The receptor may be a biological receptor. The sequence or BBD may transmit a signal to the cells, tissues or other materials associated with the biological receptor after binding, but such is not required. Examples include, but are not limited to, BBDs specific for hormone receptors, neurotransmitter receptors, cell surface receptors, enzyme receptors and antibody-antigen systems. The BBD may thus be either an agonist or antagonist, or a mixed agonist-antagonist. The BBD may also include any ligand for site-specific RNA or DNA binding, such as sequences which may be employed as mimics of transcription and other gene regulatory proteins. The BBD may also include any sequence of one or more amino acids or mimetics, or other constrained molecular regions, which exhibit binding to a biological receptor found on other peptides, on enzymes, antibodies, or other compositions, including proteinaceous compositions, which may themselves exhibit binding to another biological receptor. A peptide or peptidomimetic complexed to a metal ion with such a BBD constitutes a member of a "specific binding pair," which specific binding pair is made up of at least two different molecules, where one molecule has an area on the surface or in a cavity which specifically binds to a particular spatial and polar organization of the other molecule. Frequently, the members of a specific binding pair are referred to as ligand and receptor or anti-ligand. Examples of specific binding pairs include antibody-antigen pairs, hormone-receptor pairs, peptide-receptor pairs, enzyme-receptor pairs, carbohydrate-protein pairs (glycoproteins), carbohydrate-fat pairs (glycolipids), lectin-carbohydrate pairs and the like.

The BBD is further defined to include the portion of a construct, wherein the construct is a peptidomimetic, peptide-like, or metallo-construct molecule, which upon binding of the construct with a metal ion, is biologically active, exhibiting binding to a biological receptor found on cells, tissues, organs and other biological materials. The BBD may, in this instance, be sychnological or rhegnylogical, and generally has the attributes and functions of a BBD of a peptide. The BBD may be coextensive with all or a portion of the MBD, so that the same amino acids or other residues which constitute the MBD also constitute all or a part of the BBD. In some instances, one or amino acids of the MBD will form a part of the BBD, and one or more additional amino acids, which are not part of the MBD, form the remainder of the BBD.

Conformational constraint refers to the stability and preferred conformation of the three-dimensional shape assumed by a peptide or other construct. Conformational constraints include local constraints, involving restricting the conformational mobility of a single residue in a peptide; regional constraints, involving restricting the conformational mobility of a group of residues, which residues may form some secondary structural unit; and global constraints, involving the entire peptide structure. See generally *Synthetic Peptides: A User's Guide*, cited above.

The primary structure of a peptide is its amino acid sequence. The secondary structure deals with the conformation of the peptide backbone and the folding up of the segments of the peptide into regular structures such as α-helices, β-sheets, turns and the like. Thus, the three-dimensional shape assumed by a peptide is directly related to its secondary structure. See generally *Synthetic Peptides: A User's Guide*, cited above, including the text, figures and tables set forth at pages 24-33, 39-41 and 58-67. A global structure refers to a peptide structure which exhibits a preference for adopting a conformationally constrained three-dimensional shape.

The product resulting from the methods set forth herein can be used for both medical applications and veterinary applications. Typically, the product is used in humans, but may also be used in other mammals. The term "patient" is intended to denote a mammalian individual, and is so used throughout the specification and in the claims. The primary applications of this invention involve human patients, but this invention may be applied to laboratory, farm, zoo, wildlife, pet, sport or other animals. The products of this invention may optionally employ radionuclide ions, which may be used for diagnostic imaging purposes or for radiotherapeutic purposes.

Peptide and Metallo-Construct Molecule Libraries and Combinatorial Chemistries. Using the methods of this invention, libraries of peptides and peptidomimetics are designed wherein each constituent library member includes an MBD sequence necessary for providing a coordination site for complexation with a metal, it being understood that such sequence may differ among the constituent members of the library. Upon complexing the MBD with a metal, a specific structure results, forming a mimic of a reverse turn structure. The specific stereochemical features of this complex are due to the stereochemistry of the coordination sphere of the complexing metal ion. Thus the preferred geometry of the coordination sphere of the metal dictates and defines the nature and extent of conformational restriction.

Libraries of this invention contain constituents which are either locally or globally constrained structures. Libraries may include molecules with either local conformation restrictions or global conformation restrictions, or some combination thereof. This aspect of the invention includes a variety of methods of synthesis, screening and structural elucidation of positive hits in screening systems. The importance of these aspects are well known to those skilled in the art and will also become evident from the following description and examples.

In general, most of the metals that may prove useful in this invention have a coordination number of 4 to 6, and rarely as high as 8, which implies that the putative MBD must be made of residues with reactive groups located in a stereocompatible manner so as to establish a bond with a metal ion of given geometry and coordination sphere. Coordinating groups in the peptide chain include nitrogen atoms of amine, amide, imidazole, or guanidino functionalities; sulfur atoms of thiols or disulfides; and oxygen atoms of hydroxy, phenolic, carbonyl, or carboxyl functionalities. In addition, the peptide chain or individual amino acids can be chemically altered to include a coordinating group, such as oxime, hydrazino, sulfhydryl, phosphate, cyano, pyridino, piperidino, or morpholino groups. For a metal with a coordination number of 4, a tetrapeptide amino acid sequence may be employed (such as Gly-Gly-Gly-Gly) (SEQ ID NO:1), or a tripeptide amino acid sequence in which at least one of the amino acids has a side chain with a coordinating group can similarly be employed (such as Gly-Gly-Cys). The side chain can have a nitrogen, oxygen or sulfur-based coordination group. Thus, an amino acid sequence can provide an $N_4$, $N_3S$, $N_2S_2$, $NS_3$, $N_2SO$ or similar ligand, yielding tetradentate coordination of a metal ion utilizing nitrogen, sulfur and oxygen atoms.

In another embodiment of the invention, the MBD includes one or more amino acid residues and one or more derivatized amino acids or spacer sequences, with the derivatized amino acid or spacer sequence having a nitrogen, sulfur or oxygen atom available for complexing with the various oxidation states of the metal Examples of derivatized amino acids include amide, primary alkyl or aryl amide, 1,2,3,4-tetrahydroisoquinoline-2-carboxylic acid and its corresponding 7-hydroxy derivative, N-carboxymethylated amino acids, 2'-mercapto-Trp, $N^\beta$-(2 mercaptoethane)-α,β-diaminopropionic acid and similar higher homologs of other homologous amino acids, $N^\beta$-(2 aminoethane)-α,β-diaminopropionic acid and similar higher homologs of other homologous amino acids, $N^\beta$-(picolinoyl)-α,β-diaminopropionic acid and similar higher homologs of other homologous amino acids, α-(picolylamide)-Asp and similar homologs of other homologous amino acids, $N^\beta$-(2-amino-benzoyl)-α,β-diaminopropionic acid and similar higher homologs of other homologous amino acids, α-(2-amidomethylpyridine)-Asp and similar homologs of other homologous amino acids, N-benzyloxycarbonyl amino acid, N-tert butyloxycarbonyl amino acid, N-fluorenylmethyloxycarbonyl amino acid and other similar urethane-protected amino acid derivatives, and other derivatized or synthetic amino acids relating to any of the foregoing. Examples of spacer sequences which may be employed in this invention include 2-mercaptoethylamine, succinic acid, glutaric acid, 2-mercaptosuccinic acid, ethylenediamine, diethylenetriamine, triethylenetetraamine, tetraethylenepentaamine, glycol, polyethylene glycol, thioglycolic acid, mercaptopropionic acid, pyridine-2-carboxylate, picolylamine, 2-mercaptoaniline, 2-aminobenzoic acid, and 2-aminomethylpyridine. In general, any sequence which may be linked, directly or indirectly, to one or two amino acids so as to form a continuous sequence, and which has a nitrogen, sulfur or oxygen atom available for complexing with the valences of the metal ion, may be employed as an element of the MBD.

S-Protected Thiol Group Compounds in Metallo-Libraries. A free thiol (SH) group is preferred for complexation of most metal ions to the peptides and peptidomimetics of this invention, and in many cases an SH group is necessary in order to form a stable exchange-inert complex with a metal. Peptides and other organic molecules with free SH groups, however, are easily oxidized in air and in solution, and can often form a disulfide-linked dimer. If more than one free SH group is present in a molecule, oxidation may lead to a complex polymer. Similarly, if a mixture of different peptides or organic molecules with free SH groups are prepared, oxidation generally leads to a complex mixture of polymers of unknown composition. This is of serious concern in preparing libraries of metallopeptides or other organic molecules where one or more SH group is intended for use in metal complexation.

A variety of SH protecting groups have been employed for a variety of purposes, including radiopharmaceutical manufacture and formulation. For example, in its protected form S-Benzoyl-mercaptoacetyl-glycyl-glycyl-glycine (Bz-MAG$_3$) has been used to complex $^{99m}$Tc under conditions where the S-Bz group splits during $^{99m}$Tc complexation. The use of S-Bz protection, however, is not compatible with the methods of peptide synthesis. See, e.g., European Patent Applications 0,250,013 and 0,173,424.

In order to construct metallopeptide libraries of this invention which incorporate an SH group, if mixed pool synthesis is employed the peptides must be S-protected derivatives. The SH protecting group is chosen such that (a) the synthesis of peptide derivatives with S-protecting group is compatible with methods of solution and solid phase peptide synthesis, so that the S-protecting group is stable during synthetic procedures, and (b) the S-protecting group can be deprotected in situ, without cleavage from the resin in the case of solid phase synthesis, during the metal complexation step. Many prior art methods, such as Bz-MAG$_3$, meet at most only one of the two criteria specified above (Bz-MAG$_3$ meets only criterion (a) above.

Use of orthogonally S-protected thiol groups permits synthesis of metallo-compounds in a single pot. A mixture of compounds, each compound containing an orthogonal S-protected group ("OSPG"), is used for complexation with a metal ion, and it is only during metal ion complexation that the S-protected group is deprotected, and accordingly polymerization and cross-linking is avoided.

This procedure thus provides homogenous libraries of metallo-compounds. One OSPG meeting the criteria specified above, and which can be used in this invention, employs an S$^t$Bu (S-thio-butyl or S-t-butyl) group to protect the SH group. The S$^t$Bu group is stable under both the acidic and basic conditions typically employed in peptide synthesis. Further, the S$^t$Bu group may be cleaved by reduction using a suitable phosphine reagent, which reduction step may be employed immediately prior to or in conjunction with complexation of a metal ion to the peptide. Such OSPG cleavage does not cleave the peptide from the resin, or otherwise alter the structure of the peptide.

Another OSPG meeting the criteria specified above and suitable for this invention employs an S-Acm (S-acetamidomethyl) group to protect the SH group. The Acm group is also stable under the acid and base conditions usually employed during peptide synthesis. The S-Acm group may be removed by treatment of S-Acm-protected peptide or peptide resin with mercury (II) acetate or silver (I) tertrafluoroborate, which liberates the thiol peptide in its mercury or silver ion-complexed state. Free thiol-containing peptide can then be recovered by treating the mercury or silver ion and thiol complexed salts with an excess of a thiol-containing reagent, such as beta-mercaptoethanol or dithiothreitol. The resulting peptide is then used for metal complexation. Alternatively, the mercury or silver ion and thiol complexed peptide may be directly treated with a metal ion complexing reagent to form the desired metallopeptide.

Other examples of OSPGs for metallopeptides include 4-methoxytrityl (Mmt), 3-nitro-2-pyridinesulfenyl (Npys) and S-sulfonate (SO$_3$H). Mmt is selectively removed upon treatment with 1% TFA in dichloromethane. Npys and S-sulfonate are selectively removed by treatment with a thiol-containing reagent such as beta-mercaptoethanol or dithiothreitol or a phosphine reagent such as tributyl phosphine. The Npys group (R. G. Simmonds R G et al: *Int J Peptide Protein Res*, 43:363, 1994) is compatible with Boc chemistry for peptide synthesis and the S-sulfonate (Maugras I et al: *Int J Peptide Protein Res*, 45:152, 1995) is compatible with both Fmoc and Boc chemistries. Similar OSPGs derived from homologous series of S-alkyl, or S-aryl, or S-aralkyl may also be used in this invention. A primary characterization of the OSPG is that its use results in the formation of a disulfide (S—S) bond utilizing one sulfur atom each from the thiol-containing amino acid and the protecting group. In addition, the resulting disulfide (S—S) bond is cleavable by the use of any of a variety of disulfide cleaving agents, including but not limited to phosphine- and thiol-containing reagents.

The method employing S$^t$Bu protected SH groups, or other OSPGs, may be employed for the generation of either solid phase or soluble libraries. For solid phase libraries, peptides may be synthesized by use of conventional Fmoc chemistry. In the case of conventional Fmoc chemistry, Fmoc-L-Cys-(S$^t$Bu) is coupled to an appropriate resin, via one or more intermediate amino acids, and additional amino acids are thereafter coupled to the L-Cys-(S$^t$Bu) residue. S$^t$Bu may be employed with either L- or D-Cys, and any of a variety of other amino acids, including designer or unnatural amino acids and mimics thereof, characterized by an SH group available for binding to a metal ion, including, but not limited to, 3-mercapto phenylananine and other related 3-mercapto amino acids such as 3-mercapto valine (penicillamine); 2-mercaptoacetic acid; 3-mercaptopropionic acid; 2-mercaptopropionic acid; 3-mercapto-3,3,-dimethyl propionic acid; 3-mercapto,3-methyl propionic acid; 3-mercapto-3,3,-diethyl proprionic acid; 2-mercapto,2-methyl acetic acid; 3-cyclopentamethlene,3-mercaptopropionic acid; 2-cyclopentamethlene,2-mercaptoacetic acid and related amino acids. In all these cases, S-protection can be by S-Bu$^t$, S-Acm, Mmt, Npys, S-sulfonate and related groups, as described above.

Metal Ion Complexation to MBD. The complexation of metal ions to the sequences in a library, and specifically to the MBD, is achieved by mixing the sequences with the metal ion. This is conveniently done in solution, with the solution including an appropriate buffer. In one approach, the metal ion is, when mixed with the peptide or peptidomimetic constituents, already in the oxidation state most preferred for complexing to the MBD. Some metal ions are complexed in their most stable oxidation state, such as calcium (II), potassium (I), indium (III), manganese (II), copper (II), zinc (II) and other metals. In other instances, the metal must be reduced to a lower oxidation state in order to be complexed to the MBD. This is true of ferrous, ferric, stannous, stannic, technetiumoxo[V], pertechnetate, rheniumoxo[V], perrhenate and other similar metal ions. Reduction may be performed prior to mixing with the sequences, simultaneously with mixing with the sequences, or subsequent to mixing with the sequences. Any means of reduction of metal ions to the desired oxidation state known to the art may be employed.

For tetradentate coordination with a metal ion, rhenium is a preferred ion. Solid phase resin bound peptide or peptidomimetic sequences may be labeled with rhenium ion by treatment with the rhenium transfer agent ReOCl$_3$(PPh$_3$)$_2$ in the presence of 1,8-Diazabicyclo[5,4,0]undec-7-ene as a base. The sequences may then be cleaved from the resin. Alternatively, peptide or peptidomimetic sequences in a soluble library may similarly be labeled by treatment with the rhenium transfer agent ReOCl$_3$(PPh$_3$)$_2$ in the presence of 1,8-Diazabicyclo[5,4,0]undec-7-ene as a base. Metal complexation in the presence of 1,8-Diazabicyclo[5,4,0]undec-7-ene (DBU) as a base can conveniently be accomplished at ambient room temperature.

In an alternative method of metal complexation a mild base, such as sodium acetate, can be used. In this case the thiol-containing sequence, either in solution or bound to solid phase, is taken in a suitable solvent, such as DMF, NMP, MeOH, DCM or a mixture thereof, and heated to 60-70EC with the rhenium transfer agent ReOCl$_3$(PPh$_3$)$_2$ in the presence of sodium acetate for 15 minutes. Similarly, other bases such as triethylamine, ammonium hydroxide and so on, may be employed. According to this invention, MeOH is a preferred choice of solvent for rhenium complexation in the case of S-deprotected peptides in solution. The solvent choice for S-deprotected peptides still attached to the solid phase is guided mainly by considerations of superior solvation (swelling) of the solid phase. DMF and NMP may be employed. Various mixtures of these solvents, also in combination with MeOH, and DCM, CHCl$_3$ and so on, may also be employed to yield optimized complexation results.

In one embodiment of this invention, an S-Bu$^t$ protected peptide is treated in situ with rhenium transfer agent in the presence of DBU and tributylphosphine to effect S-deprotection and rhenium complexation in one pot. Alternately, complexation of rhenium to the S-Bu$^t$ protected peptide in the presence of rhenium perrhenate may be accomplished by treatment with Sn[II]Cl$_2$. This reagent effects S-deprotection as well as conversion of ReO$_4$ state to ReO state in situ to cause complexation of the rhenium to the S-deprotected peptide. A preferred procedure in this invention is the use of S-Bu$^t$ protected peptide with S-deprotection by treatment with tributylphosphine, and metal complexation of the resulting peptide utilizing ReOCl$_3$(PPh$_3$)$_2$ in the presence of DBU at room temperature.

In the libraries of this invention, the MBD forms a reverse turn structure upon complexation with a metal ion, with the library constructed such that side chains of amino acids within the MBD are varied, and similarly amino acids not forming a part of the MBD are also varied. Various compounds in a library of metallopeptides can be obtained by varying the sequence of amino acids in a set of peptides that are all optimized to form a complex of nearly similar geometry when coordinated with a metal ion. This optimization can be obtained, for example, by appropriate positioning of amino acids having high affinity to complex a metal ion. Examples of naturally occurring amino acids with high affinity for metal complexation include Cys and His. A library of such peptides, therefore, would have at least one of these amino acids that is suitably placed in the sequence, with this amino acid being common to all the molecules in the library, with this amino acid thus non-randomized.

A conceptual, generalized view of a solid phase library of metallopeptides that is constructed using local conformational restriction is:

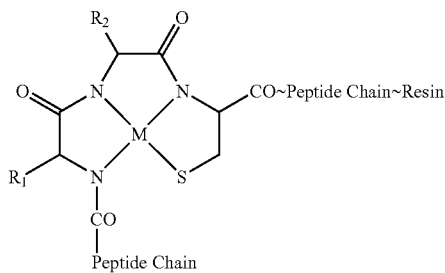

where M is a metal ion, $R_1$ and $R_2$ are randomly selected amino acid side chains forming parts of the reverse turn structure which is the BBD, and "Peptide Chain" denotes one or more amino acids. A similar library can also be constructed in which the components are soluble, and thus not bound to a resin.

One illustration of a locally restricted metallopeptide library, in which the members are conformationally constrained upon metal ion complexation, is a library directed towards the family of various integrin receptors that recognize the RGD sequence. In this library, individual amino acid positions are degenerated by selecting a set of cationic amino acids for one position, a second set of anionic amino acids for another position and a third set of selected amino acids with strong metal complexation properties. Other positions in the peptides are randomized. The common rigid structure of the metal-peptide complex in this library allows for various forms of presentation of the cationic and anionic centers for interaction with the integrin receptors. A library of these structures can be employed to identify metallopeptides specific to individual integrin receptors. The general structure of this library, which can either be soluble or solid-phase library, prior to metal ion complexation is:

$R_1$-Aaa-Bbb-Ccc-Ddd-$R_2$, where $R_2$ is coupled to a resin for solid phase bound libraries, and where Aaa is an L- or D-configuration residue providing an N for metal ion complexation, such as Arg, Lys, Orn, homoArg, 2,3-diamino propionic acid, 2,4,-diaminobutyric acid, S-aminoethyl cysteine, 3(O-aminotheyl) Ser, or another synthetic basic amino acids;

Bbb is an L- or D-configuration residue providing an N for metal ion complexation, such as Gly, Ala, Aib, Val, Nle, Leu or similar amino acids with uncharged side chains;

Ccc is an L- or D-configuration residue providing both an N and S, or alternatively two Ns, available for metal ion complexation, such as Cys, HomoCys, Pen, or other amino acids, natural or unnatural, containing both an N and S, together with an OSPG, available for metal ion binding;

Ddd is an L- or D-configuration residue with a negatively charged side chain functional group, such as Asp, Glu, or synthetic amino acids with a negatively charged side chain functional group; and $R_1$ and $R_2$ are H, Alkyl, aryl, alkylcarbonyl, arylcarbonyl, alkyloxycarbonyl, aryloxycarbonyl, or a polymer such as PEG, PVA, or polyamino acid, attached directly or through a carbonyl group.

Other forms of this library include sets of structures with general formulas shown below, wherein the spatial distances between the cationic and anionic centers can be different than those shown above, such as of the formulas:

$R_1$-Bbb-Aaa-Ccc-Ddd-$R_2$, $R_1$-Bbb-Ddd-Ccc-Aaa-$R_2$, or $R_1$-Ddd-Bbb-Ccc-Aaa-$R_2$.

For each of the foregoing, the definitions of $R_1$, $R_2$, Aaa, Bbb, Ccc and Ddd are as described above. All four classes of libraries described above can either be synthesized individually or prepared as one library.

Another embodiment of this invention provides for construction of a library with global conformational restriction. In this embodiment, the MBD can be held constant, and a randomized or selected series of sequences of amino acids or mimetics varied to form the library. This type of library encompasses metallopeptides in which a MBD is an isosteric replacement for a disulfide, lactam, lactone, thioether or thioester moiety in cyclic peptides. In these constructs a set MBD is introduced between two pre-selected ends of a linear peptide or peptidomimetic that contains the randomized or selected series of sequences of amino acids or mimetics under investigation. The general structure of a metallopeptide library of this type is:

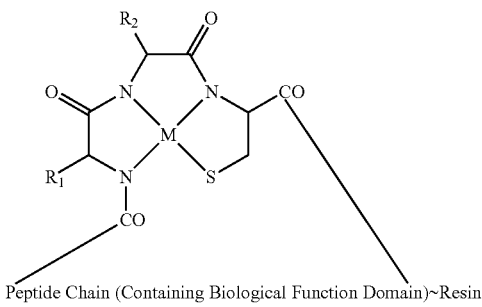

Peptide Chain (Containing Biological Function Domain)~Resin where M is a metal ion and $R_1$ and $R_2$ are structural elements that may provide additional stability to metal complexation, or may modulate biological activity, such as determining the organ of clearance, or altering biodistribution patterns or pharmacokinetics. The "Peptide Chain" sequence may be randomly varied, thereby resulting in a random library, or may be directed in a predetermined fashion, based upon known characteristics of the target molecule.

One illustration of a globally-constrained metallopeptide library is a library of peptides wherein all the individual members of the library include a metal ion-binding domain and the library is directed specifically towards a family of peptide hormones, such as somatostatin, cholecystokinin, opioid peptides, melanotropins, luteinizing hormone releasing hormone, tachykinins and similar peptide hormones. The general formula of this library of peptides, before complexation to a metal ion, is:

$R_1$-Aaa-Baa-Caa-$R_2$~Resin where X is a fixed MBD including a plurality of amino acids, so that all of the valences of the metal ion are satisfied upon complexation of the metal ion with X, $R_1$ and $R_2$ each comprise from 0 to about 20 amino acids, and Aaa, Baa and Caa each comprise one or more amino acids connected to X through an amide, thioether, thioester, ester, carbamate, or urethane bond, wherein each of Aaa, Baa, and Caa is varied. In this example, the MBD may include an OSPG. Other thiols in the sequence may optionally include S-protecting groups that are not orthogonal, such that the OSPG may be removed without removal of other S-protecting groups in the sequence.

For solid phase libraries the peptide constructs are attached to a resin, and the resin is omitted for soluble libraries. This library of globally constrained metallopeptides can also be screened for detecting compounds that are mimetics for various peptides that are known to exist in a reversed turn structure as their hypothesized biologically active structure. The examples of these include various peptide hormones such as somatostatin, cholecystokinin, opioid peptides, melanotropins, luteinizing hormone releasing hormone, tachykinins and various antibody epitopes.

The functional equivalent of each these peptide libraries may also be obtained through the development of a library of non-amino acid building blocks so as to result in structural mimics of these peptides. The peptide bonds may be replaced by pseudopeptide bonds, such as thioamides, thioethers, substituted amines, carbanate, urethane, aliphatic moieties, and functionally similar constructs.

A peptide library is first assembled according to the sequence specification and degeneration, as described above, by well-known methods of peptide synthesis. These libraries can be synthesized as discreet, spatially addressable compounds in parallel synthesis, using split synthesis approaches, or by deconvolution techniques of soluble libraries. Using similar methods, a pseudopeptide, peptidomimetic or non-peptide library can be obtained. The non-peptide libraries may also optionally incorporate one of various tagging approaches that are well known to those skilled in the art. Both solid-phase and soluble libraries can be obtained in this manner. The entire library is then reacted with an appropriate metal-complexing agent to obtain the corresponding metal-coordinated library, comprising a similar class of predetermined structures. For example, to complex a peptide library with rheniumoxo metal ion, the peptide library can be treated with $Re(O)Cl_3(PPh_3)_2$ in the presence of sodium acetate. This procedure results in quantitative complexation of ReO with the peptide. In order to complex Zn, Co, Mn, Fe or Cu ions, the peptide library is treated with chloride or other suitable salts of these metal ions to yield the library of corresponding metal ions. Essentially, a variety of metal ions can be used to construct different metallopeptide libraries. One limiting factor in selection of the appropriate metal ion is the relative stability of a particular metal-peptide complex, related in large part to the metal-peptide binding constant or constants. It is well known in the art that some metal-peptide constructs are stable only within specified pH or other special conditions, or are easily oxidized in air. Some peptide-metal ion complexes, such as those with ReO, are stable in pure form and can be isolated and stored under normal storage conditions for a long period of time.

A metallopeptide library constructed according to this invention can be screened to identify one or more receptor-binding or pharmacologically-active candidates by various techniques that have been reported in the prior art. Both soluble and solid phase libraries may be directly employed in these assays. These techniques include direct target binding approaches as described by Lam and coworkers (Lam K S et al: *Nature* 354:82-84, 1991; Lam K S et al: *Nature* 360:768, 1992), deconvolution and iterative re-synthesis approaches (Houghten R A et al: *Proc Natl Acad Sci USA* 82:5131-5135, 1985; Berg et al: *J Am Chem Soc* 111:8024-8026, 1989; Dooley C T et al: *Science* 266:2019-2022, 1994; Blondelle S E: *Antimicrob Agents Chemother* 38:2280-2286, 1994; Panilla C: *Biopolymers* 37:221-240, 1995), approaches using orthogonal pools of two co-synthesized libraries according to Tartar and coworkers (Deprez B et al: *J Am Chem Soc* 117: 5405-5406, 1995), positional scanning methods devised by Houghton and coworkers that eliminate iterative re-synthesis (Dooley C T et al: *Life Sci* 52:1509-1517, 1993; Pinilla C et al: *Biotechniques* 13:901-905, 1992; Pinilla C et al: *Drug Dev Res* 33:133-145, 1992), and a combination of the positional scanning method with split synthesis methods (Erb E et al: *Proc Natl Acad Sci USA*, 91:11422-11426, 1994).

Among these techniques, the deconvolution and iterative resynthesis approach, the approach involving orthogonal pools of two co-synthesized libraries, and the positional scanning method may be directly applied to soluble metallopeptide libraries to elucidate the structure of a "hit," or peptide identified as a receptor-binding or pharmacologically-active candidate in the screening process. For solid phase libraries, other than spatially addressable parallel synthesis libraries, the structure of hits can be directly determined by various strategies well known to those skilled in the art. These include direct mass spectrometric analysis of compounds covalently bound to solid phase matrix of particles by the use of matrix-assisted laser desorption/ionization (MALDI) techniques (Siuzdak G et al: *Bioorg Med Chem Lett* 6:979, 1996; Brown B B et al: *Molecular Diversity* 1:4-12, 1995). The technique of creating a series of partially end-capped compounds at each of the synthetic steps during library assembly also helps in unambiguous identification by mass spectrometry (Youngquist R S et al: *J Am Chem Soc*, 117:3900-3906, 1995; Youngquist R S et al: *Rapid Commun Mass Spectr* 8:77-81, 1994). In addition to these analytical techniques, various encoding strategies that have been devised for structure elucidation in organic molecule-based libraries, including non-peptide and non-nucleotide libraries, may be utilized. Various encoding strategies, such as DNA encoding, peptide encoding, haloaromatic tag encoding, and encoding based on radiofrequency transponders, are now well known in the art and can be used directly in combination with metallopeptide libraries. These tagging strategies require the incorporation of the tags during the course of synthesis of libraries, which can be accomplished during the construction of a metallopeptide libraries, since metal complexation is a final, post-synthesis step.

Structural Diversity of Library Members. Examples of some of the molecular templates which may be employed in this invention are shown in FIG. 1. These templates show the appropriate location of R groups required to make a molecule selective and potent for a given biological target. The templates of FIGS. 1A, 1H and 1J allow introduction of as many as 7 to 8 different functional groups. The templates of FIGS. 1B and 1C allow introduction of as few as four functional groups. The templates are derived from both peptide and non-peptide polyamine backbones, and may be partly peptidic and partly non-peptidic in nature. The metal coordination sphere illustrated in these templates is either an $N_3S$ or an $N_2S_2$ configuration where N and S are the metal coordinating atoms.

Using the methods of this invention, that portion of the template forming a constrained sequence upon metal ion complexation can have attached thereto a wide variety of functional groups, which groups may be attached by any means known. The ten structures depicted at FIG. 1A through 1J are for illustration purposes only, and in no way limit the scope of this invention. Other structures may be employed, including a variety of linking groups. In addition, different structures are employed with metal ions requiring other than tetradentate coordination.

Figure 1B:
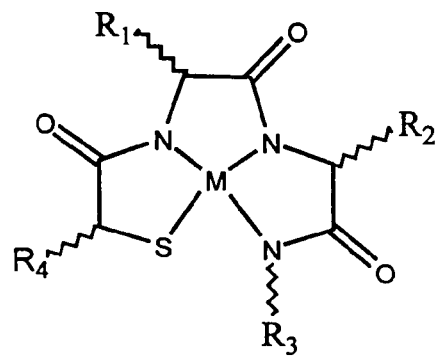
Figure 1C:
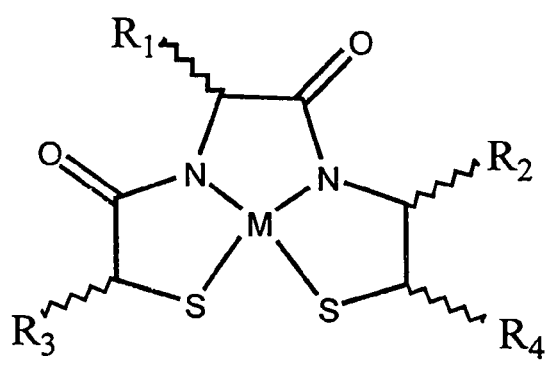
Figure 1D:
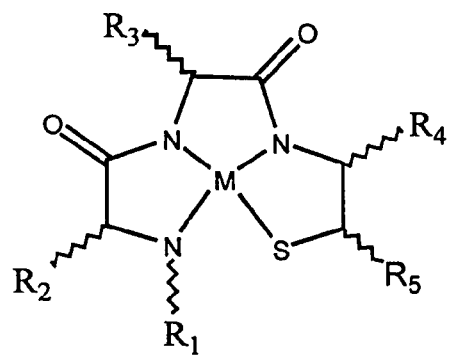
Figure 1E:
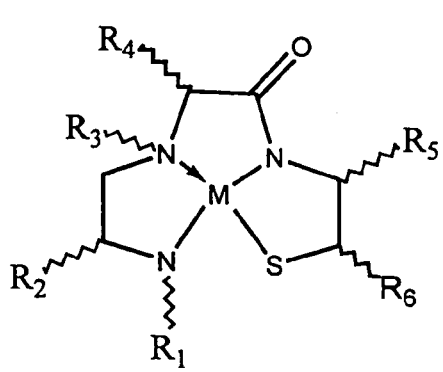
Figure 1F:
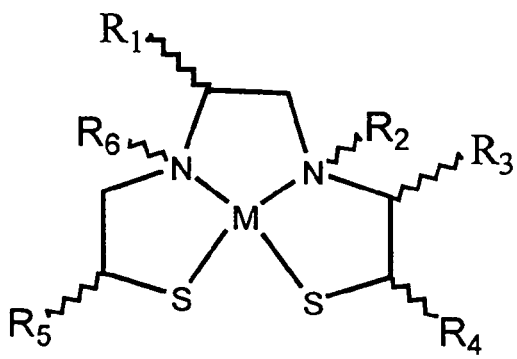

The templates shown in FIGS. 1A through 1J, and other templates which may be created based upon the methods of this invention, allow for inclusion of as many as seven or eight different functional groups. These different functional groups may either individually or in combination impart desired affinity, specificity, selectivity, potency, and pharmacological and pharmacokinetic profiles to the molecule towards a biological target. For example, the structure depicted in FIG. 1D is obtained by complexation of a metal ion "M" with a linear peptide. The sulfur "S" atom for complexation to "M" is provided by the side chain of a Cys amino acid residue. The functional groups $R_2$, $R_3$, and $R_4$ may be side chains of amino acids. $R_1$ may also be an amino acid or an organic group, while $R_5$ may be a beta-substitution in the Cys residue.

Figure 1G:
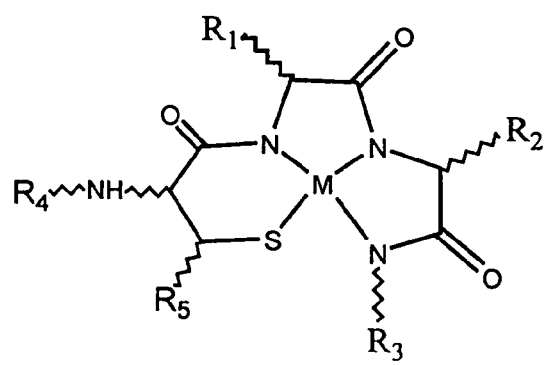
Figure 1H:
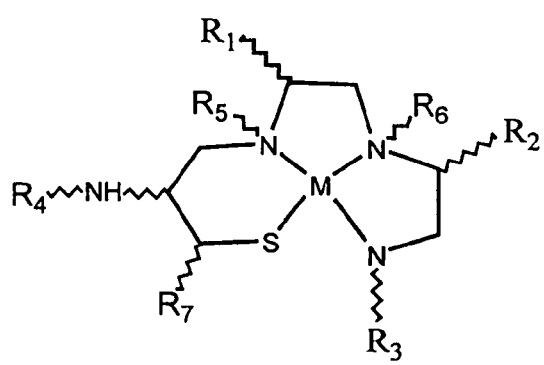
Figure 1I:
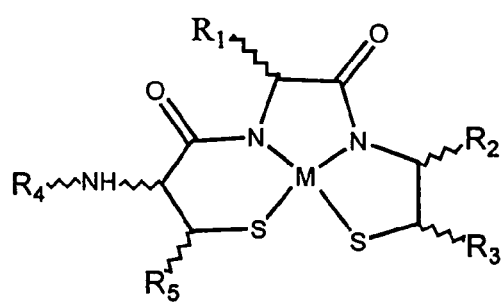
Figure 1J:
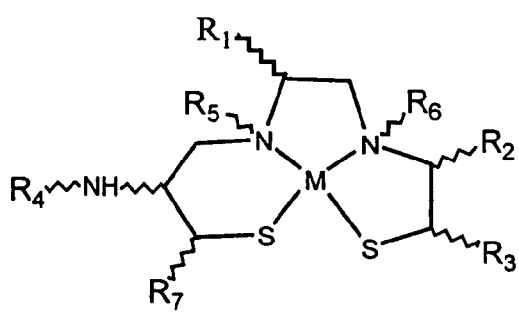

The structure depicted in FIG. 1B is derived from a linear peptide chain in which β-substituted β-mercaptoacetic acid has been substituted at the N-terminus. The structure depicted in FIG. 1G is similar to that of FIG. 1B, except that mercaptoacetic acid is substituted for Cys. The structure depicted in FIG. 1G offers a different topographic structural relationship of the side chain functionalities $R_1$, $R_2$, $R_3$ and $R_4$ from that of the structure depicted in FIG. 1B. These kinds of minor, yet potentially biologically important, differences in structure may result in different affinities, specificities, selectivities or potencies. The five structures depicted in FIGS. 1B, 1C, 1D, 1G and 1I can be obtained from the corresponding linear peptide derivatives synthesized by common methods well known to those skilled in the art. Complexation of metal ion to these linear peptides can be accomplished on solid phase or solution phase using the methods discussed above.

The structures of FIGS. 1A, 1F, 1H, 1J and 1E are derived from the structures of FIGS. 1B, 1C, 1D, 1G and 1I by reducing one or more "M" complexing amide bonds (CO—NH group) to a pseudopeptide bond ($CH_2$—NH group), followed by the functionalization of the resulting amine nitrogen with an "R" group. These reduced amide bond molecules, therefore, allow the introduction of additional "R" groups in the molecule to enhance the structural diversity and complexity of the molecules. The "N" complexation to the "M" in these cases is through the formation of a coordinate bond. Such molecules have different charge characteristics than the amide "N" complexed molecules. Differences of this type in the core charge of metal complexes are known to alter the passage of metal complexes across the biological compartment barriers. For example, $^{99m}$Tc-MAG$_3$ (mercaptoacetylglycylglycylglycine), with an ionic core charge of −1, is not compartmentalized and is excreted through the kidneys, while $^{99m}$Tc-MIBI (methoxyisobutylisonitrile), with an ionic core charge of +1, is compartmentalized in heart muscles. $^{99m}$Tc-HMPAO (hexamethylpropyleneamine oxime) and $^{99m}$Tc-ECD (ethyl cysteinate dimer), each with no charge, pass through the blood-brain barrier and are used as brain perfusion imaging agents. Thus in one aspect of this invention libraries may be constructed with differences in ionic charges, as is generally shown in FIG. 1, by providing either an amide "N" or an amine "N" to modulate the pharmacokinetic profile of library members. Synthesis of reduced amide bond molecules capable of providing an amine "N" may be accomplished by employing methods of making linear peptide derivatives with pesudopeptide bonds that are well known to those skilled in the art. See, for example, Wen J J and Spatola A F: *J Peptide Res* 49:3-14, 1997.

In yet another aspect of this invention, libraries may be constructed wherein a variety of metal ions "M" are used for complexation. In the structures depicted in FIG. 1, metal ions requiring tetradentate coordination are most applicable, so that "M" may be a metal ion such as Tc or Re. However, use of all other metal ions is contemplated and possible, and in such case, it is also contemplated and possible that other structures would be employed, providing for hexadentate or other coordination spheres. Further, "M" may be a metal ion (M), a metal-oxo group (M=O), a metal-nitride group (M/N), or an N-nitrido substituted metal-nitride or organoimido (M=N—$R^1$). The organoimido M=N—$R^1$ species allows for inclusion of an $R^1$ which may act as a biologically significant functional group similar to the various R groups described in the structures of FIG. 1. In this case, the size of the library may be expanded by substitution of different R' groups.

The metal-oxo compounds may be obtained from a suitable pre-formed metal-oxo transfer agent such as Re(O)Cl$_ $(PPh$_3$)$_2$ (Johnson N P et al: *Inorg Syntheses* 9:145-148, 1967; Parshall G: *Inorg Synth* 17:110, 1977; and Sullivan B P et al: *Inorg Syntheses* 29:146-150, 1992). Metal-oxo compounds may also be obtained by direct reduction of rhenium perrhenate with stannous or another suitable reducing agent in the presence of the complexing molecule, thereby yielding a metal-oxo complex (Rouschias G: *Chemical Review* 74:531-566, 1974; and Vites J C and Lynam M M: *Coordination Chemistry Review* 142:1-20, 1995).

Nitrido complexes can be prepared by several methods. See, for example, the method taught in U.S. Pat. No. 5,288,476; U.S. Pat. No. 5,300,278; Sullivan B P et al: cited above; Rouschias G: cited above; Vites J C and Lynam M M: cited above; Dehnicke K and Strahle J: *Angew Chem Int Ed Engl,* 31:955-978, 1992; Baldas J: *Inorganic Chem* 25:150-153, 1986; and Marchi A et al: *Inorganic Chem* 29:2091-2096, 1986. In general, the nitrido complexes can be obtained by treating a rhenium oxo complex with a hydrazine or by the use of $Re(N)Cl_2(PPh_3)_2$ as a transfer agent.

The organoimido M=N—R' species may be prepared by condensing a rhenium oxo complex with a primary amine, or with 1,2 disubstituted hydrazines, or with phosphinimines or with phenyl isocyanate (Rouschias G: *Chemical Review,* 74:531-566, 1974). The rhenium oxo, rhenium nitrido and rhenium organoimido complexes are extremely stable and are reported to persist through fairly drastic substitution reactions.

The functionalized sulfydryl-containing templates may be synthesized from corresponding halogenated compounds by treating them with sodium thiosulfate to form S-sulfonate salts. These salts, on treatment with a reducing agent such as tributyl phosphine or sodium borohydride, yield a functionalized sulfhydryl. Alternatively, S-sulfonate derivatives can directly be used in the synthesis of metallo-compounds as discussed above. In this case, the S-sulfonate group also acts as a OSPG in both the solution phase and the solid phase synthesis of metallo-constructs using either Boc or Fmoc chemistries. The S-sulfonate OSPG may be selectively removed by treatment with a tributyl or triisopropyl phosphine immediately prior to the complexation of the metal ion.

The structures of FIGS. 1A through 1J, and similar structures, may be used in libraries by selective substitution of any or all of $R_1$ through $R_7$. It is also possible and contemplated that different related structures of any of FIGS. 1A through 1J, or similar structures, may be used in libraries, while keeping the functionalities of $R_1$ through $R_7$ constant.

The invention is further illustrated by the following non-limiting examples.

EXAMPLE 1

Single-Pot Synthesis of Four-Member $N_3S_1$ Type Metallopeptide Compound Library A SynPep multiple peptide synthesizer was used for synthesis of the peptides on solid phasing using convention Fmoc chemistry. Fmoc-L-Glu-($O^tBu$)-Wang resin (1.2 g, 0.54 mM) was swollen in NMP and the Fmoc-group removed by adding 20% piperidine in NMP and mixing by bubbling nitrogen for 20 min. The solvent was drained by suction and the resin washed. Four equivalent of Fmoc-L-Cys-($S^tBu$)-OH (0.93 g), four equivalent of 2-(1H-Benzotriazol-1-yl)-1,1,3,3-tetramethyluronium (TBTU) and six equivalent of diisopropylethylamine (DIEA) were added with NMP and bubbled with nitrogen for 30 min. The resin was again washed and deprotection of the Fmoc-group repeated, yielding $NH_2$-L-Cys-($S^tBu$)-L-Glu-($O^tBu$)-Wang resin. The resin was then split into two pools, and using similar methods Fmoc-L-Gln-(Trt)-OH was added to one pool and Fmoc-D-Gln-(Trt)-OH added to the other pool. The two pools were mixed and the Fmoc-group deprotected, yielding $NH_2$-(L,D)-Gln-(Trt)-L-Cys-($S^tBu$)-L-Glu-($O^tBu$)-Wang resin. The resin was again split into two pools, and Fmoc-L-Asn-(Trt)-OH added to one pool and Fmoc-D-Asn-(Trt)-OH added to the other pool. The two pools were mixed and the Fmoc-group deprotected, yielding $NH_2$-(L,D)-Asn-(Trt)-(L,D)-Gln-(Trt)-L-Cys-($S^tBu$)-L-Glu-($O^tBu$)-Wang resin. To this resin was added 0.072 g of succinic anhydride in pyridine, yielding $HOOC(CH_2)_2CONH$-(L,D)-Asn-(Trt)-(L,D)-Gln-(Trt)-L-Cys-($S^tBu$)-L-Glu-($O^tBu$)-Wang resin. After washing, the $S^tBu$ group was removed by adding 13.8 mL of DMF/Tributylphosphine (20/3, v/v; 0.52 M) and bubbling for 3 hours. The resulting resin was again washed, yielding $HOOC(CH_2)_2CONH$-(L,D)-Asn-(Trt)-(L, D)-Gln-(Trt)-L-Cys-L-Glu-($O^tBu$)-Wang resin. 0.6 g of $ReO(PPh_3)_2Cl_3$ (8 eq.) and 0.32 g of sodium acetate (final 1 M) were added to the resin solution, and the solution heated at 70EC for 2 hours. After cooling to room temperature, the resin was washed and dried, and 3 mL of a TFA "cocktail" (5% water, 5% TIPS, 5% thioanisole and 85% TFA) was added. The solution was allowed to stand for 3 hours. The resin was then filtered and washed once with 1 mL of TFA. Cold ether was added to the collected TFA solution, and the resulting precipitate was washed with cold ether and dried under high vacuum. The resulting mixture was a gray colored solid that weighed 40 mg, a yield of approximately 56%, and which contained equal quantities of $HOOC(CH_2)_2CONH$-L-Asn-(Trt)-L-Gln-(Trt)-L-Cys-L-Glu (SEQ ID NO:2); $HOOC(CH_2)_2CONH$-L-Asn-(Trt)-D-Gln-(Trt)-L-Cys-L-Glu; $HOOC(CH_2)_2CONH$-D-Asn-(Trt)-L-Gln-(Trt)-L-Cys-L-Glu; and $HOOC(CH_2)_2CON$ H-D-Asn-(Trt)-D-Gln-(Trt)-L-Cys-L-Glu.

EXAMPLE 2

Alternate Single-Pot Synthesis of Four Member $N_3S_1$ Type Metallopeptide Compound Library 1,8-diazabicyclo[5,4,0]undec-7-ene (DBU) as alternative base, replacing sodium acetate. The peptide $HOOC(CH_2)_2CONH$-L-Asn-(Trt)-L-Gln-(Trt)-L-Cys-L-Glu-$O^tBu$ (SEQ ID NO:2) attached to Wang resin was mixed with 1,8-diazabicyclo(5,4,0]undec-7-ene (DBU) (8 eq.) and $ReO(PPh_3)_2Cl_3$ (8 eq.) in DMF. The reaction was carried out at room temperature for 4 hours. The subsequent cleavage of product from the resin, washing and precipitation was as described for Example 1 above.

EXAMPLE 3

In Situ Formation of Metallo-Complexes in the Presence of Reducing Agent and $ReO(PPh_3)_2Cl_3$ The resin $HOOC(CH_2)_2CONH$-(L, D)-Asn-(Trt)-(L, D)-Gln-(Trt)-L-Cys-($S^tBu$)-L-Glu-($O^tBu$)-Wang obtained from Example 1 above was mixed with tributylphosphine (0.52 M) and $ReO(PPh_3)_2Cl_3$ (8 eq.) in DMF. The bases used in the reaction were either sodium acetate (0.1 M) or 1,8-diazabicyclo(5,4,0]undec-7-ene (DBU) (8 eq.). In the case of sodium acetate, the reaction was conducted at about 70EC for 4 hours. In the case of DBU, the reaction container was shaken at room temperature for 4 hours. The subsequent cleavage of product from the resin, washing and precipitation was as described for Example 1 above.

EXAMPLE 4

Synthesis of Ac-His-X-Cys-Trp-$NH_2$ (SEQ ID NO:3)—Rhenium Complexes with PEG Resin (Where X=Trp, Homophe, 2-NaI, or Phenylglycine)

The procedures were similar to those described for Examples 1, 2 and 3. A NovaSyn TGR resin was used. Histidine, Cysteine and Tryptophan were protected by trityl, thio-t-butyl and Boc groups, respectively. The cleavage cocktail was TFA/TIS (95/5). After three hours the resin was filtered and washed with TFA. To the TFA solution was added cold ether, and the resulting precipitate was spun down by centrifugation. The resulting pellets were washed with ether twice, and 0.5 mL of 95% acetic acid was added. Five mL of water was added after one hour. The resulting product was then lyophilized under high vacuum.

EXAMPLE 5

Development of a Prototype Metallopeptide Library for the Melanocortin Receptor The library design was based on the tetrapeptide message sequence, His-Phe-Arg-Trp (SEQ ID NO:4) (6-9 sequence), of α-MSH. This sequence exists as a reverse turn, making it suitable for conversion into a metallopeptide format of this invention. In this approach metallopeptides were designed around a tripeptide $N_3S_1$ MBD designed for a rhenium metal ion. The MBD was derivatized to yield the pentapeptide Ac-His-Phe-Arg-Cys-Trp-$NH_2$ (SEQ ID NO:5) as a putative candidate for melanocortin ("MC") receptors. Further refinements in the structure were made in response to other considerations, including the chirality of amino acid side chains, yielding a template structure Ac-His-D-Phe-Arg-Cys-Trp-$NH_2$. The structure of this peptide after binding to rhenium is:

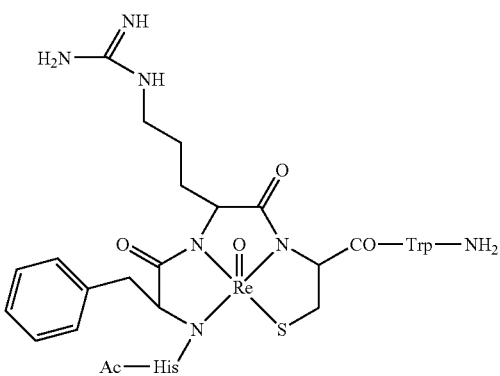

The template structure was used to define a small combinatorial library utilizing split synthesis methodologies. The final template selected for the combinatorial library was Ac-D-His-Xaa-D-Cys-Trp-$NH_2$, where Xaa was D-(2') Naphthylalanine, D-Trp, D-HomoPhe, or D-Phenylglycine. For this library, the peptide resin, Cys(S$^t$Bu)-Trp(Boc)-Resin was split in four equal parts. Each part was reacted with one of the four Xaa types. After coupling, the resin pools were mixed and synthesis continued in a single pool to couple the His residue. The final result was four separate peptides in a single pool, each peptide varying by one amino acid, in the Xaa position.

An S$^t$Bu OSPG group was used to protect the SH group during synthesis. After solid-phase assembly of the peptide chain using Fmoc chemistry with acid labile side chain protecting groups, the S$^t$Bu group was split using tributylphosphine. The resulting free SH-containing peptide-resin was treated with the rhenium transfer agent Re(O)Cl$_3$(PPh$_3$)$_2$ in the presence of 1,8-Diazabicyclo[5,4,0]undec-7-ene as base. The resulting metallopeptide resin was then treated with TFA to cleave it from the resin and de-protect all the side chain protecting groups. The products were analyzed by mass spectrometry. HPLC analysis was performed and individual peaks collected and subjected to mass analysis. The resulting peptides were analyzed by electron spray mass spectrometry, yielding the predicted mass, including the rhenium complexed to the peptide.

EXAMPLE 6

Design and Synthesis of Melanocortin Receptor—Specific Metallopeptide Library The library was rationally designed based upon data relating to melanocortin receptors and peptide sequences specific to the melanocortin receptors, including melanotropin side-chain pharmacophores, D-Phe[7] and Trp[9], that interact with a hydrophobic network of receptor aromatic residues in transmembrane regions 4, 5, 6, and 7. Based on this design criterions, a pharmacophore for the melanocortin receptor was preliminarily defined, and a combinatorial library designed for identification of potent and receptor-selective agonists.

Based on the design criteria, the putative structure R-Aaa-Baa-L-Cys-Caa-$NH_2$ was selected, in which each of Aaa, Baa and Caa are selected from L- or D-isomers of 2-NaI (1), Phe (2), Trp (3), Tyr (4) and Ala (5), so that any one of the foregoing can be substituted for any one of Aaa, Baa or Caa. In the nomenclature adopted for the library design, the five amino acids were designated 1 through 5, with the isomerism conventionally notated, so that, for example, Baa$_2$L refers to L-Phe in the Baa position.

The terminal R group was selected from Ac, $C_6H_{500}H$, $CH_3(CH_2)_5$—COOH, $C_6H_5CH$=CH—COOH (trans) and Pyridine-3-carboxylate. The terminal R group represents a truncated amino acid, and offers additional structural diversity.

A pool and split library synthesis scheme was employed such that 5,000 separate compounds were synthesized, resulting in 200 final pools each containing 25 different compounds, with the compounds differing solely by the amino acids in the Aaa and Baa position. Using this methodology, binding characteristics relating to the Caa amino acid or R terminal group can be identified through inter-group comparison, thereby simplifying the deconvolution strategy.

Figure 5:
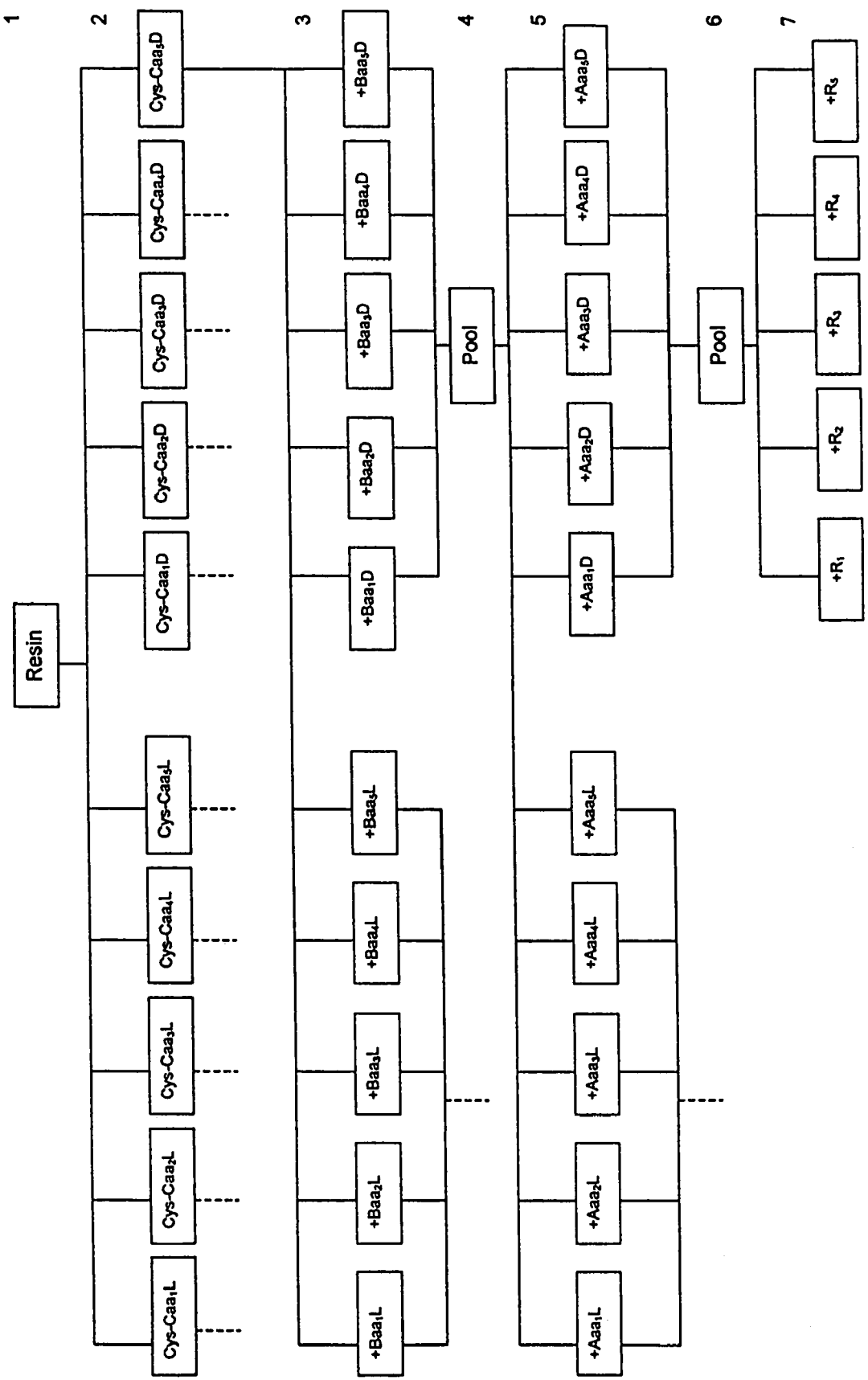
FIG. 5 Flow chart of a split pool and combination synthesis method according to Example 6.

The library synthesis steps are set forth in FIG. 5. The resin of step 1 was divided into 10 groups. At step 2 each of Caa$_1$L through Caa$_5$D were coupled to an individual resin group, and L-Cys was coupled to each resin group, resulting in 10 groups and 20 couplings. Each of the resin groups of step 2 was then divided into 10 sub-groups as shown at step 3 (with only one subgroup illustrated at step 3, and for each subgroup of step 3, each of Baa$_1$L through Baa$_5$D were coupled to one group within the subgroup, resulting in 100 groups in 10 subgroups and 100 couplings. For each subgroup of step 3, the five Baa$_x$L members and the five Baa$_x$D members were separately pooled in step 4, resulting in 20 subgroups, with each subgroup containing five different sequences differing by the Baa$_x$ member. Each of the 20 subgroups of step 4 were then in step 5 divided into 10 groups (with only one shown for illustration purposes in FIG. 5), and for each subgroup, each of Aaa$_1$L through Aaa$_5$D were coupled to one group within the subgroup, resulting in 200 groups in 20 subgroups and 200 couplings. For each subgroup of step 5, the five Aaa$_x$L members and the five Aaa$_x$D members were separately pooled in step 6, resulting in 40 subgroups, with each subgroup containing twenty-five different sequences differing by the Baa$_x$ and Aaa$_x$ member. In step 7, each of the 40 subgroups of step 6 were divided into five groups, and each of R$_1$ through R$_5$ were coupled to one group within the subgroup, resulting in 200 groups in 40 subgroups, with each group containing 25 different sequences differing by the $Baa_x$ and $Aaa_x$ member.

Peptides were synthesized using Fmoc chemistry, with side chain functionalities protected using acid labile groups. The SH group of the Cys residue was protected by a $S^tBu$ OSPG cleavable in presence of both base and acid labile groups using tributylphosphine as the reducing agent. The peptide chain was assembled on the solid phase using 1-(1H-benzotriazole-1-yl)-1,1,3,3,-tetra-methyluronium tetrafluoroborate (TBTU) as a coupling agent. The SH group was then selectively unprotected and rhenium metal ion complexed using the rhenium transfer agent $Re(O)Cl_3(PPh_3)_2$ in the presence of 1,8-Diazabicyclo[5,4,0]undec-7-ene (DBU) as base. In this manner, the metal-peptide complex was formed with the peptide chain still tethered to the solid support. The metallopeptide was then liberated from the solid support by treatment with TFA. This solid phase approach to metal ion complexation is fully compatible with split synthesis methodologies employed in combinatorial libraries.

The synthesis process was performed using commercial automated synthesizers. Multiple manual synthesizers (such as those commercially available from SynPep Corporation, Dublin, Calif.) allow parallel synthesis of ten peptides simultaneously.

Figure 2:
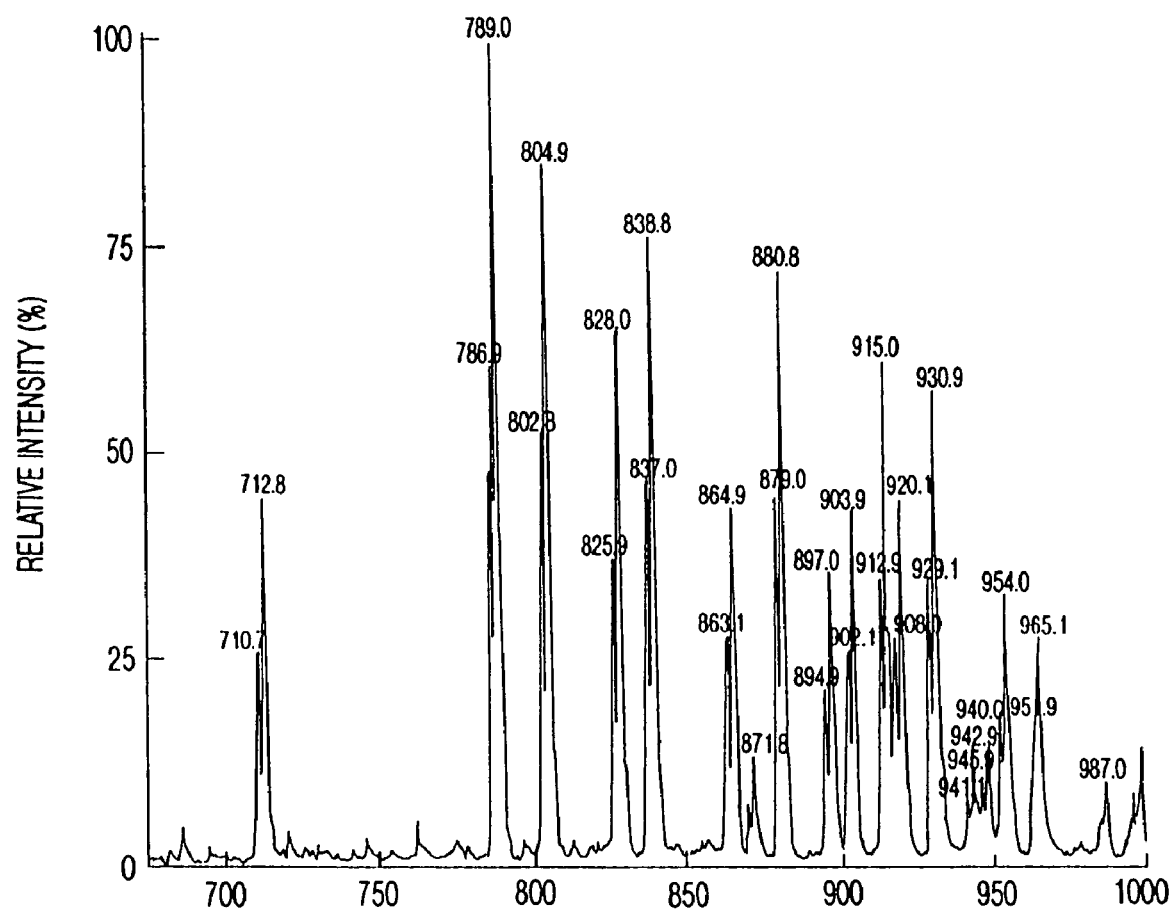
FIG. 2 Mass spectrum of a library pool of 25 metallopeptides synthesized according to Example 6.

Quality control protocols were employed as required, and include HPLC, mass spectral analysis, and amino acid analysis on each individual pool of 25 compounds. The presence of each of pool constituent is established by molecular ion mass spectral analysis. Negative ion mode electron spray (ES) and matrix-assisted laser desorption (MALDI) techniques were employed. Using mass spectral analysis, three different measures were made: (a) the presence of up to 25 individual compounds by molecular ion peak measurement (assuming different masses for each compound), (b) confirmation that the molecular ion peaks show complexation to a rhenium metal ion, and (c) absence of peaks with molecular masses corresponding to peptides uncomplexed with metal ion. Rhenium is a mixture of two isotopes that differ in mass by 2 units (186 and 188) with a relative abundance of these isotopes of 1:2. The molecular ion profile of a metallopeptide appears as two peaks that differ by 2 mass units with integrated area ratios of 1:2. Rhenium thus acts as an internal mass spectral reference for these metallopeptides. A spectral analysis of one such pool of 25 compounds synthesized by the methods of this claim is shown at FIG. 2. Five sets of two metallopeptides in this pool have similar masses due to the presence of the same amino acids assembled in different sequences. The relative intensities of the peaks is due to differential ionization of individual compounds in the pool and does not reflect the relative amounts in the mixture. Each pair of peaks with mass unit differences of 2 and relative ratios of 1:2 are due to the relative abundance of two stable isotopes of rhenium (Re-185 and Re-187). The spectral analysis did not reveal any free uncomplexed linear peptides, which would be approximately 197 to 199 mass units less than the corresponding metallopeptide, due to the absence of the rhenium-oxo core.

Amino acid analysis of each pool of 25 metallopeptides was also employed, and was used to determine the relative equimolar ratio of each of 25 compounds in a pool. The synthetic protocols of split synthesis were designed to assure equimolar amounts of pool constituents.

EXAMPLE 7

Screening of Melanocortin Receptor—Specific Library

Metallopeptide library pools are screened for MC4 receptor and MC1-R receptor binding activity in high throughput screening assays. The MC receptor-binding assay uses membrane preparations from B16-F1 melanoma cells as the source of MC receptor. Cell membranes prepared from MC-4 receptor-expressing 293 cells and negative control, untransfected 293 cells, are substituted for B16-F1 melanoma cell membranes in MC-4 receptor specific binding assays. The MC receptor-binding assays use the Millipore Multi-Screen System and are performed in 96-well Millipore filter plates (Durapore, 0.45 μm porosity) pre-blocked with 0.5% bovine serum albumin in phosphate buffered saline. Cell membrane preparations (12.5 μg/well) are incubated with 0.4 nM $^{125}$I-NDP-MSH in HEPES Buffer containing 0.2% bovine serum albumin. Non-specific binding is determined by addition of $10^{-6}$ M α-MSH or $10^{-7}$ M NDP-MSH. Metallopeptides to be tested are added to reaction wells at a final concentration of 1 mM. After incubation for 90 min at room temperature, the binding reaction is rapidly terminated by filtration to capture the membranes. Filters are washed 3 times with ice-cold PBS and air-dried. Individual filters are then punched from the plates and distributed into gamma counter tubes. Radioactivity associated with the membranes is determined in a Packard Cobra gamma counter. Specific binding is determined as the radioactivity in wells containing $^{125}$I-NDP-MSH alone minus the radioactivity in wells containing $10^{-6}$M α-MSH. Test compounds are screened in duplicate wells and are considered to be active where 1 μM concentrations inhibit >50% of the specific binding. Standard curves of unlabeled NDP-MSH will be included on each plate as an internal assay control.

A commercially available cAMP kit (R&D Systems, DE0350, low pH) is employed to evaluate agonist potential of metallopeptides that bind to MC-4 receptor. 293 cells stably transfected with hMC-4 receptor, or B16-F1 melanoma cells, are grown to confluence in 96-well dishes. Cells are washed and fresh RPMI containing 0.2 mM isobutylmethylxanthine (cAMP phosphodiesterase) and varying concentrations of metallopeptides, or α-MSH as a positive control, are added, and the cells are incubated for 1 hr at 37° C. Medium is aspirated, and cell layers extracted with 150 μl of 0.1 M HCl. Total cAMP accumulation in 100 μl of cell extract is quantitated in 96-well plates by competitive immunoassay with the cAMP kit, using an acetylation modification. $EC_{50}$ values for test compounds will be calculated based on cAMP accumulation in cells treated with $10^{-6}$M α-MSH. The capabilities of both of these cell types to accumulate cAMP in the presence of α-MSH and MSH analog peptides are documented in the scientific literature cited in Example 1 and Ollman M M et al: *Science* 278:135-138, 1997.

EXAMPLE 8

Deconvolution of Melanocortin Receptor—Specific Library

Deconvolution of a positive pool is done by iterative re-synthesis and screening deconvolution approaches. The individual 25 constituents are synthesized separately, or alternatively in 5 smaller pools of 5 compounds each, with each pool screened in receptor binding assays. The latter approach is preferred where there is a high hit frequency in the preliminary screen. The compounds in pools with the best results (closest to receptor affinity in the nanomolar range and MC4 to MC-1 receptor selectivity of at least 100) are individually synthesized and screened.

EXAMPLE 9

Alternative Method of Deconvolution of Melanocortin Receptor—Specific Library In this example, an alternative method of mass spectral deconvolution of metallopeptide libraries is employed. The method is based on the internal signature of rhenium-complexed peptides (two isotopic peaks in 1:2 ratios differing by 2 mass units), which generally permits metallopeptide identification even in mixed solutions. A positive pool is incubated with receptor-bearing cells, the excess unbound compounds washed away under controlled conditions, and the cells treated with a solvent to disrupt metallopeptide binding and extract the metallopeptide in the solvent. Mass spectral analysis of the solvent reveals the metallopeptide or metallopeptides which are bound to the receptor-bearing cells, and through comparison to the quality control data it is possible to ascertain the specific metallopeptide or metallopeptides which are bound. This process provides high throughput of metallopeptide library screening.

EXAMPLE 10

Single Pot Synthesis of a Library of Four Metallopeptides of the General Structure Ac-His-Xaa-Cys-Trp-NH$_2$ A synthesis procedure similar to that described in Example 1 was used in making this library. A NovaSyn TGR resin for making peptide amides (substitution 0.2 mM/gm) was used. Fmoc synthetic strategy was employed using the following protected amino acids: Fmoc-Trp(Boc), Fmoc-Cys(SBu$^t$), Fmoc-Xxx, and Fmoc-His(Trityl). The Xaa amino acids were Trp, HomoPhe, 2'-Naphthylalanine, and Phenylglycine. The peptide resin Cys(Bu$^t$)-Trp-NH$_2$ was split into four equal pools and one of the Xaa amino acids was coupled to one individual pool. After completion of the coupling reaction, the four resin pools were mixed again. The synthesis proceeded with the coupling of His followed by acetylation of the N-terminus. After the complete assembly of the peptide chain Ac-His(Trt)-Xaa-Cys(S-Bu$^t$)-Trp(Boc)-NH$_2$, the S-Bu$^t$ OSPG group was removed by treatment with DMF/tributylphosphine and rhenium-oxo metal ion was complexed as generally described in Example 1. The fully protected metallopeptide was deblocked and liberated from the solid support by treatment with a cleavage cocktail (95:5 mixture of trifluoroacetic acid-triisopropylsilane) for three hours. The metallopeptide library was recovered by precipitation using cold ether. The resulting pellet was washed twice and 0.5 ml of 95% acetic acid was added. After one-half hour 5 ml of water was added and the solution was freeze-dried yielding the desired library in solid form. Mass spectrometric analysis of the library pool confirmed the correct masses for all four members of the library:

| Compound | Structure | Calculated Mass | Mass (M + 1) found |
|---|---|---|---|
| 1 | Ac-His-Phg-Cys-Trp-NH$_2$ (SEQ ID NO: 6) | 815.7 and 817.6 | 815.2 and 816.7 |
| 2 | Ac-His-Trp-Cys-Trp-NH$_2$ (SEQ ID NO: 7) | 868.8 and 870.7 | 868.0 and 870.1 |
| 3 | Ac-His-HPhe-Cys-Trp-NH$_2$ (SEQ ID NO: 8) | 843.8 and 845.7 | 842.8 and 845.2 |
| 4 | Ac-His-2'Nal-Cys-Trp-NH$_2$ (SEQ ID NO: 9) | 880.0 and 881.9 | 879.1 and 880.9 |

Figure 3:
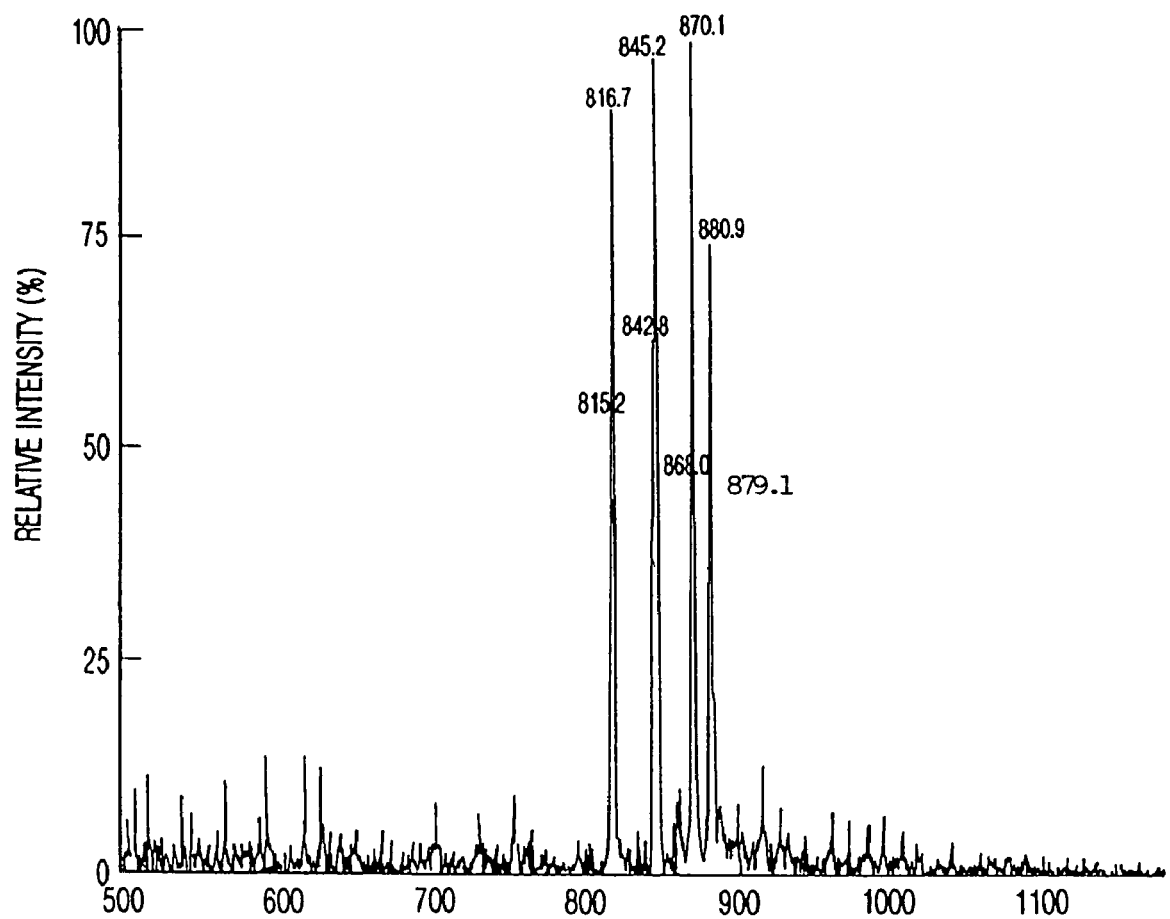
FIG. 3 Mass spectrum of a library pool of 4 metallopeptides synthesized according to Example 10.
Figure 4:
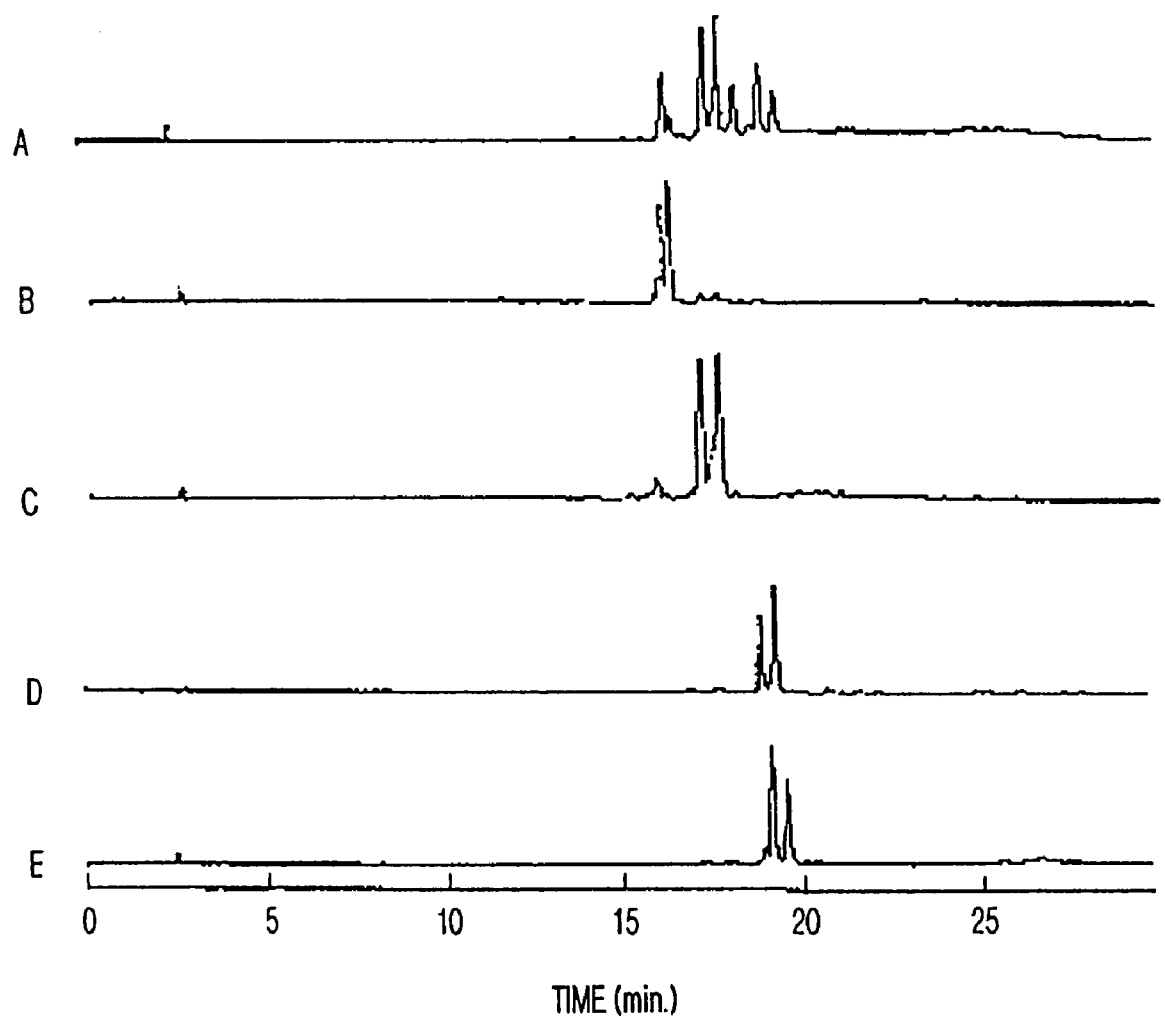
FIGS. 4A-4E Reversed phased HPLC profiles of a library pool of 4 metallopeptides synthesized according to Example 10.

As noted in the table, two molecular ion peaks differing in mass units of 2 were calculated and observed for each structure; this difference is presumptively due to the presence of two natural isotopes of rhenium, Re-185 and Re-187, in the complexation step. In addition, the area under the observed peaks in the spectrometric analysis showed that for each structure the area was in a 1:2 ratio, which is identical to and presumptively related to the relative abundance of Re-185 and Re-187 isotopes. These results confirmed the complexation of rhenium to the peptides. FIG. 3 depicts the mass spectrum of a library pool of 4 metallopeptides. The relative intensities of these peaks is due to the differential ionization of individual compounds in the pool and does not reflect the relative amounts in the pool. The spectral analysis did not reveal any free uncomplexed linear peptides, which would be approximately 197 to 199 mass units less than the corresponding metallopeptide, due to the absence of the rhenium-oxo core. FIG. 3 depicts reversed phased HPLC profiles of a library pool of 4 metallopeptides. The pool is shown in FIG. 4A, and each of the individual peptides is shown in FIGS. 4B through 4E. Each individual peak in FIGS. 4B through 4E matched HPLC profiles in the pool in FIG. 3A, showing the presence of each of the four compounds in the pool. Each individual peptide is resolved into two isomeric peaks (syn- and anti-isomers) that are due to two alternate orientations of the oxygen atom in the Re═O core. All four compounds used for this comparison were individually prepared using the methods described above for synthesis of the library. The HPLC profiles of the individual compounds are shown as FIGS. 4A to 4E.

EXAMPLE 11

Synthesis of a Small Multi-Pool Library Targeted for Human Neutrophil Elastase of the General Structure R-Aaa-Bbb-Cys-Val-NH$_2$ The library was synthesized as a 60-member library in 12 pools of 5 metallopeptides each. In each of the 12 pools only Aaa was randomized using five different structural variants, while both R and Bbb were constant for that pool. The R group was a N-terminal capping group selected from benzyloxycarbonyl, acetyl and succinyl groups. Aaa was selected from five different residues, Ala, Leu, Ile, Phe, and Lys(N-Z). Bbb was selected from Gly, Ala, Ser, and Asn. The structure of the metallopeptides in these pools is described in the Example 12.

All 12 metallopeptide pools were synthesized using the general strategy and methodology described in Examples 1, 6, and 9. Each of the pools was characterized by mass spectrometry, and shown to have the five correct masses for rhenium-complexed peptides (with two isotopic peaks in ratio of 1:2 differing by mass units of 2). Additionally the mass spectra did not show any peaks related to linear peptides not complexed to a metal ion, signifying all or substantially all of the peptide was complexed to rhenium ions.

EXAMPLE 12

Screening of 60-Membered Multi-Pool Library of the General Structure R-Aaa-Bbb-Cys-Val-NH$_2$ Targeted for Human Neutrophil Elastase Purified human neutrophil elastase (HNE) was purchased from Sigma (St. Louis, Mo.). The assay was performed spectrophotometrically using a chromogenic p-nitroanilide substrate, MeOSuc-Ala-Ala-Pro-Val-pNA, also purchased from Sigma. The assay protocols were similar to those described by others (e.g., Nakajima K et al: *J Biol Chem*, 254:4027-4032, 1979). Briefly, 0.05 units of HNE were treated with 1 mM concentration of the library pool in the presence of p-nitroanilide substrate. Spectrophotometric measurement were made at a wavelength of 410 nm. The results of the assay are shown in the following table. The screening results revealed that only three out of the 12 pools displayed inhibition below an assigned assay cutoff of 1 mM. Also, among this limited series of compounds, benzyloxycarbonyl group was identified as a preferred R group where Bbb was a Gly, Ala, or Ser residue.

The following shows the general structure ReO-[R-Aaa-Bbb-Cys-Val-NH$_2$]:

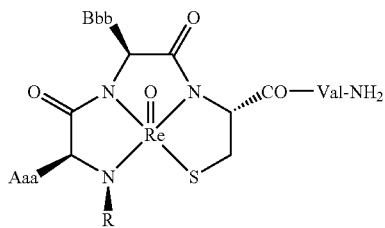

The following table shows the structure of the 60 members of the 12 pool library, where Z is benzyloxycarbonyl, Ac is acetyl and Suc is succinyl:

| Compounds per Pool | R | Aaa is one of: | Bbb | IC$_{50}$ (µM) |
|---|---|---|---|---|
| 5 | Z | Ala, Leu, Ile, Phe, Lys(N,-Z) | Ser | 385 |
| 5 | Z | Ala, Leu, Ile, Phe, Lys(N,-Z) | Ala | 625 |
| 5 | Z | Ala, Leu, Ile, Phe, Lys(N,-Z) | Asn | >1000 |
| 5 | Z | Ala, Leu, Ile, Phe, Lys(N,-Z) | Gly | 769 |
| 5 | Ac | Ala, Leu, Ile, Phe, Lys(N,-Z) | Ser | >1000 |
| 5 | Suc | Ala, Leu, Ile, Phe, Lys(N,-Z) | Ser | >1000 |
| 5 | Ac | Ala, Leu, Ile, Phe, Lys(N,-Z) | Ala | >1000 |
| 5 | Suc | Ala, Leu, Ile, Phe, Lys(N,-Z) | Ala | >1000 |
| 5 | Ac | Ala, Leu, Ile, Phe, Lys(N,-Z) | Asn | >1000 |
| 5 | Suc | Ala, Leu, Ile, Phe, Lys(N,-Z) | Asn | >1000 |
| 5 | Ac | Ala, Leu, Ile, Phe, Lys(N,-Z) | Gly | >1000 |
| 5 | Suc | Ala, Leu, Ile, Phe, Lys(N,-Z) | Gly | ~1000 |

EXAMPLE 13

Deconvolution of Library Pool of the General Structure Z-Aaa-Ser-Cys-Val-NH$_2$ Targeted for Human Neutrophil Elastase The pool with highest activity, Z-Aaa-Ser-Cys-Val-NH$_2$, was deconvoluted by an iterative resynthesis process. All five individual peptides in this pool were synthesized by the methodologies and protocols of Example 10. Each individual peptide was characterized by mass spectrometry and HPLC. A screening assay was performed as generally described in Example 11. The best results were obtained with Leu or Ile in the position Aaa in the peptide chain. The peptide Z-Leu-Ser-Cys-Val-NH$_2$ (SEQ ID NO:10) displayed an IC$_{50}$ value of 139 µM and the peptide Z-Ile-Ser-Cys-Val-NH$_2$ (SEQ ID NO:12) displayed an IC$_{50}$ value of 179 µM. Substitution of the three residues Ala, Phe, and Lys(N-Z) at Aaa yielded IC$_{50}$ values in excess of 1,000 µM. Based on these results, the two peptides Z-Leu-Ser-Cys-Val-NH$_2$ (SEQ ID NO:10) and Z-Ile-Ser-Cys-Val-NH$_2$ (SEQ ID NO:11) appeared to meet stereochemical requirements as an HNE inhibitor. The results of this assay, where Z is benzyloxycarbonyl, are shown in the following table.

| R | Aaa | Bbb | IC$_{50}$(µM) |
|---|---|---|---|
| Z | Ala | Ser | >1000 |
| Z | Leu | Ser | 139 |
| Z | Ile | Ser | 179 |
| Z | Phe | Ser | >1000 |
| Z | Lys(N,-Z) | Ser | >1000 |

EXAMPLE 14

Synthesis of —SH Containing Building Blocks from Halogenated Compounds

A variety of "S" containing building blocks (other than amino acids) for use in the synthesis of libraries according to this invention can be synthesized from corresponding halogenated congeners. The process relies on the treatment of a halogenated compound with sodium thiosulfate at slightly basic pH to obtain the corresponding Bunte salt (the S-sulfonate derivative) as described by Wunderlin R et al: *Helv Chim Acta* 68:12-22, 1985. The Bunte salt S-sulfonate derivative is treated with a reducing agent such as 2-mercaptoethane, sodium borohydride or tributyl phosphine to yield a free thiol-containing product. This product can then be S-protected with conventional S-protecting groups such as Trt, Mmt, Npys, Bu$^t$, S-Bu$^t$ known in the art of peptide synthesis. Alternatively, and preferably in this invention, the Bunte salt S-sulfonate derivative may be directly used in the synthesis of peptides as described by Maugras I et al: *Int J Peptide Protein Res* 45:152, 1995. The S-sulfonate derivative is stable using either Fmoc or Boc synthetic peptide synthesis methods, and following peptide synthesis the resulting peptide may be treated with tributyl phosphine to liberate the free —SH group. In either method, the resulting peptide has an available free thiol for complexation with a metal ion, which complexation may be according to either the solid phase or solution phase methods described above.

EXAMPLE 15

Synthesis of Reduced Peptide Bond Metallopeptide Library

Metallopeptide libraries may be synthesized wherein the library members contain either a reduced peptide bond or an N-substituted reduced peptide bond, such that the library members contain a CH$_2$—NH group or CH$_2$—NR group rather than a CO—NH peptide bond. Examples of these structures are given at FIGS. 1A, 1D, 1E, 1H and 1J. The synthetic methods employed are similar to those for metallopeptides containing solely peptide bonds. The compounds are produced by the methods of this invention using either solution phase or solid phase synthesis. In general, the synthetic strategy involves assembling a linear peptide derivative incorporating a reduced peptide bond, as is generally discussed in Wen J and Spatola A F: *J Peptide Res* 49:3-14, 1997. In the synthesis strategy, an orthogonal S-protecting group is employed that is compatible with the reductive alkylation step during the introduction of a pseudopeptide bond. For example, a Mmt (4-methoxytritryl) group may be used for S-protection during Fmoc synthetic strategy. The Mmt group is released upon treatment with 1% TFA in dichloromethane without cleaving the peptide from the resin, such that solid phase metal ion complexation may be employed. As necessary, means to provide orthogonal protection of the amine functionality of the reduced peptide bond ($CH_2NH$) generated during the introduction of the reduced peptide bond may also be employed. One group that may be employed to provided orthogonal protection of the amine functionality is the Dde group [1-(4,4-Dimethylaminophenylazo)benzoyl] which is stable during both Fmoc and Boc cleavage conditions and is selectively removed by treatment with 2% hydrazine in DMF for 2-5 minutes. Using such protecting groups, a fully assembled peptide is treated first with hydrazine to remove Dde groups and then with 1% TFA in dichloromethane to remove Mmt group from the peptide on the resin. The resulting sequence may then be complexed to a metal ion while on solid phase, and thereafter cleaved from the resin as described above.

Alternatively, the amine protection on the reduced peptide bond $CH_2NH$ group is a Boc group and the fully assembled peptide is deprotected and liberated from the resin in a single step upon treatment with TFA. Metal complexation can then be accomplished in solution as described above.

Library members containing an N-derivatized functionality such as $CH_2$—NR group rather than a CO—NH peptide bond, as shown at FIGS. 1A, 1D, 1E, 1H and 1J, may be synthesized by assembling a linear peptide with S-Mmt protection and a $CH_2NH$ amine which is N protected using a Dde group. The Ddd is then selectively removed by the treatment with hydrazine in DMF. The liberated amine is then functionalized by attachment of an R group through treatment with the corresponding halogenated derivative of the R group in the presence of a base. Following removal of the S-Mmt group by treatment with 1% TFA in dichloromethane, the resulting library member may be complexed with a metal ion as described above. Alternatively, after N-functionalization, the resulting library member can be deprotected and released cleaved from the resin in one step and the metal complexation accomplished in solution as described in above.

EXAMPLE 16

Synthesis of Library Members Providing $S_2N_2$ Metal Ion Complexation

Libraries containing members with $S_2N_2$ metal ion coordination, as shown in FIGS. 1C, 1E, 1I and 1J, may be synthesized by means similar to those employed with libraries containing members with $S_1N_3$ metal ion coordination. In one method, a second "S" is introduced in the structure by incorporating into the linear assembly of the peptide an S-protected derivative of 2-mercaptoacetic acid or Cys. The choice of S-protecting groups is guided by selection of orthogonal protection criteria described above. After the assembly of the linear peptide, the protecting groups from both of the "S" atoms is removed and metal ion complexation is accomplished as generally described above.

Alternatively, S-deprotection, and removal of any other protecting group, may be accomplished concomitantly with the cleavage of the peptide from the resin in a single step. The metal ion complexation is then achieved in solution as described above.

EXAMPLE 17

Synthesis of Rhenium[V] Nitrido Complexes

The synthesis of rhenium nitrido compounds is similar to that for corresponding rhenium oxo complexes. The use of $Re(N)Cl_2(PPh_3)_2$ transfer agent (which may be synthesized as described by Sullivan B P et al: *Inorg Syntheses* 29:146-150, 1992) instead of $Re(O)Cl_3(PPh_3)_2$ yields the corresponding nitrido complexes. As described above for rhenium oxo complexes, the corresponding nitrido compounds can be prepared either on solid phase or in solution phase. Since metal complexation is the last step in the synthesis, the assembly of linear peptide chain library members is identical to the methods described for rhenium oxo complexes. Nitrido compounds can alternatively be prepared directly from a rhenium oxo compound by treating the rhenium oxo compound with substituted hydrazines.

EXAMPLE 19

Synthesis of Rhenium Organoimido Complexes

The synthesis of rhenium organoimido complexes is achieved in several different methods. In one method, treatment of a rhenium oxo complex with a primary amine converts it to an organoimido complex. Primarily aromatic organoimido derivatives may prepared by this method. In an alternative method, treatment of rhenium oxo complexes with 1,2 disubstituted hydrazine results in the corresponding organoimido complex. Both aromatic and aliphatic organoimido complexes can be prepared in this manner. In yet another alternative method, reaction of rhenium oxo complexes with phosphinimines ($Ph_3P=NR$) yields the corresponding organoimido complexes. Besides aliphatic and aromatic organoimido complexes, this method is effective in producing aroylimido complexes (R=PhCO). In yet another alternative method, treatment of rhenium oxo complexes with phenyl ioscyanate yields the corresponding phenyl organoimido complex.

EXAMPLE 19

Site Specific Complexation of Metal Ion to a Peptide Chain by Orthogonal Protection of Sulfydryl Groups in a Peptide Sequence Where two or more sulfhydryl groups are desired in a peptide, OSPGs may be employed, together with other S-protecting groups, such that the desired thiol group may be selectively deprotected while leaving the other thiols protected. The metal ion is complexed to the deprotected thiol and subsequent to metal ion complexation the remaining protecting groups are liberated to yield the desired metallopeptide complex.

A fully protected peptide-resin containing two S-protected thiol groups (Cys residues), Fmoc-Tyr($Bu^t$)-Cys(Trt)-Gly-Phe-Cys($S^tBu$)-Wang resin, was prepared by standard solid-phase peptide synthesis means. The N-terminal Fmoc-group was removed by treatment with 20% piperidine in DMF to give the resin Tyr($Bu^t$)-Cys(Trt)-Gly-Phe-Cys($S^tBu$)-Wang resin. In this case, the Cys(Trt) group and the Cys(S'Bu) protecting groups are orthogonal to each other. While the Cys(Trt) is an acid labile group, the Cys(S'Bu) group may be removed under reductive conditions, thereby allowing selective deprotection of one thiol group. The peptide-resin was treated with tributylphosphine (0.52 M) in DMF to remove the S—S'Bu group from the Cys residue. The resin was then treated with Re(O)Cl$_3$(PPh$_3$)$_2$ (8 eq.) in the presence of DBU as base for 4 hours at room temperature to complete the formation of the ReO[V] complex with the peptide. The peptide resin was washed extensively, dried and treated with TFA/TIS (95:5) cleavage cocktail to yield the metallo-peptide. The metallo-peptide was precipitated using MeOH-ether, and the product was dried and purified by HPLC. The purified peptide was analyzed by electron spray mass spectrometry, yielding predicted mass for the metallo-peptide complex.

EXAMPLE 20

Synthesis of a Metallo-Peptide Library Containing Two "S" Groups but Utilizing Only One "S" for Site Specific Complexation of Metal Ion to a Peptide Chain by Orthogonal Protection of Sulfydryl Groups in the Peptide Sequences. Synthesis of a Library with General Structure:
Tyr-Cys-[Aaa-Phe-Cys]-ReO[V]

A library of metallo-peptides containing two "S" capable of complexing with ReO[V] core, but directing this bond formation with only one of these two "S" atoms can be synthesized as set forth above. Fully protected peptide resin Fmoc-Tyr(Bu')-Cys(Trt)-Aaa-Phe-Cys(S'Bu)-Wang resin (SEQ ID NO:12) is prepared by solid-phase methods of peptide synthesis. The "Aaa" is an alpha amino amino acid, synthetic or naturally occurring in either L- or D-isomeric form, as may be desired for the composition of individual library members. Individual compounds with different Aaa group may be synthesized in parallel for the synthesis of a parallel library of compounds. Alternatively, all compounds may be synthesized as a mixture in one pot using different "Aaa" building blocks at the coupling step for Aaa. Alternatively, the library mixture may also be synthesized by a split and pool approach as described above using various Aaa groups.

The finished peptide-resin is treated with 20% piperidine to remove the terminal Fmoc group. Treatment of the Tyr(Bu')-Cys(Trt)-Gly-Phe-Cys(S'Bu)-Wang resin (SEQ ID NO:13) thus obtained with tributylphosphine and Re(O)Cl$_3$(PPh$_3$)$_2$ in the presence of DBU can be accomplished as described above to complex the ReO metal ion specifically at the C-terminal Cys residue while leaving the Cys(Trt) residue inert. Cleavage of the metallo-peptide resin may be accomplished as described above, and the Cys(Trt) group may be thereafter deprotected.

Each of the foregoing is merely illustrative, and other equivalent embodiments are possible and contemplated.

Although this invention has been described with reference to these preferred embodiments, other embodiments can achieve the same results. Variations and modifications of the present invention will be obvious to those skilled in the art and it is intended to cover in the appended claims all such modifications and equivalents. The entire disclosures of all applications, patents, and publications cited above are hereby incorporated by reference.

The preceding examples can be repeated with similar success by substituting the generically or specifically described reactants and/or operating conditions of this invention for those used in the preceding examples.

What is claimed is:

1. A method for producing substantially pure metallopeptides, comprising the steps of:

(a) synthesizing a sequence of the formula Aaa-MBD-Baa cleavably bound to solid phase, wherein
MBD is a metal ion-binding domain consisting of three amino acid residues with two of said residues each comprising a backbone nitrogen atom available to complex with the coordination sphere of a metal ion, the metal ion to be provided, and with one of said residues comprising a backbone nitrogen atom available to complex with the coordination sphere of a metal ion and a side chain comprising one sulfur atom protected by an orthogonal S-protecting group compatible with peptide solid phase synthesis and removable without cleaving the peptide from solid phase, such that the sequence is of the structure:

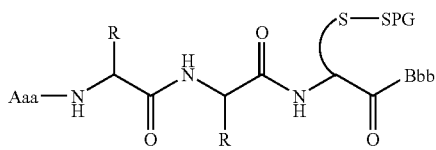

where:
Aaa and Baa each comprise from 0 to about 20 amino acid residues, provided that at least one of Aaa and Baa comprise at least 1 amino acid residue and the sequence is cleavably bound to solid phase through Aaa or Bbb,
SPG is an orthogonal S-protecting group bound to a sulfur atom forming a part of an amino acid side chain, and
R is in each instance independently hydrogen or an amino acid side chain;

(b) in a single pot, deprotecting the sulfur atom protected by an orthogonal S-protecting group by cleaving the said orthogonal S-protecting group without cleaving the sequence from the solid phase and complexing a metal ion to the MBD; and (c) cleaving the sequences from the solid phase, thereby providing a metallopeptide of the structure:

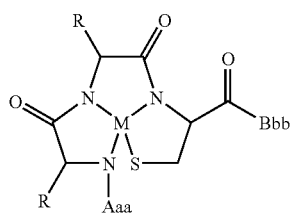

wherein
Aaa, Bbb and R are as defined above and M is a tetradentate metal ion, metal-oxo group, metal-nitride group or N-nitrido substituted metal-nitride.

2. The method of claim 1 wherein M is rhenium, rhenium-oxo, rhenium-nitride or N-nitrido-substituted rhenium-nitride.

3. The method of claim 1 wherein at least one of R is a side chain of an L- or D-isomer of 2-Nal, Phe, Trp, Tyr or Ala.

4. The method of claim 1 wherein the orthogonal sulfur atom-protecting group is S-thio-butyl, acetamidomethyl, 4-methoxytrityl, S-sulfonate or 3-nitro-2-pyridinesulfenyl.

* * * * *

SEQUENCE LISTING

```
<160> NUMBER OF SEQ ID NOS: 13

<210> SEQ ID NO 1
<211> LENGTH: 4
<212> TYPE: PRT
<213> ORGANISM: artificial
<220> FEATURE:
<223> OTHER INFORMATION: tetrapeptide metal ion binding sequence

<400> SEQUENCE: 1

Gly Gly Gly Gly
1

<210> SEQ ID NO 2
<211> LENGTH: 4
<212> TYPE: PRT
<213> ORGANISM: artificial
<220> FEATURE:
<223> OTHER INFORMATION: single-pot metallopeptide library member

<400> SEQUENCE: 2

Asn Gln Cys Glu
1

<210> SEQ ID NO 3
<211> LENGTH: 4
<212> TYPE: PRT
<213> ORGANISM: artificial
```

```
<220> FEATURE:
<223> OTHER INFORMATION: single-pot metallopeptide library member
<220> FEATURE:
<221> NAME/KEY: misc_feature
<222> LOCATION: (2)..(2)
<223> OTHER INFORMATION: Xaa is Trp, HomoPhe, 2'-Nal or Phg

<400> SEQUENCE: 3

His Xaa Cys Trp
1

<210> SEQ ID NO 4
<211> LENGTH: 4
<212> TYPE: PRT
<213> ORGANISM: artificial
<220> FEATURE:
<223> OTHER INFORMATION: tetrapeptide message sequence of alpha-MSH

<400> SEQUENCE: 4

His Phe Arg Trp
1

<210> SEQ ID NO 5
<211> LENGTH: 5
<212> TYPE: PRT
<213> ORGANISM: artificial
<220> FEATURE:
<223> OTHER INFORMATION: melanocortin-receptor specific metallopeptide
      sequence

<400> SEQUENCE: 5

His Phe Arg Cys Trp
1               5

<210> SEQ ID NO 6
<211> LENGTH: 4
<212> TYPE: PRT
<213> ORGANISM: artificial
<220> FEATURE:
<223> OTHER INFORMATION: metallopeptide library member
<220> FEATURE:
<221> NAME/KEY: misc_feature
<222> LOCATION: (2)..(2)
<223> OTHER INFORMATION: Xaa is Phelylglycine

<400> SEQUENCE: 6

His Xaa Cys Trp
1

<210> SEQ ID NO 7
<211> LENGTH: 4
<212> TYPE: PRT
<213> ORGANISM: artificial
<220> FEATURE:
<223> OTHER INFORMATION: metallopeptide library member

<400> SEQUENCE: 7

His Trp Cys Trp
1

<210> SEQ ID NO 8
<211> LENGTH: 4
<212> TYPE: PRT
<213> ORGANISM: artificial
<220> FEATURE:
<223> OTHER INFORMATION: metallopeptide library member
<220> FEATURE:
<221> NAME/KEY: misc_feature
<222> LOCATION: (2)..(2)
```

```
<223> OTHER INFORMATION: Xaa is HomoPhe

<400> SEQUENCE: 8

His Xaa Cys Trp
1

<210> SEQ ID NO 9
<211> LENGTH: 4
<212> TYPE: PRT
<213> ORGANISM: artificial
<220> FEATURE:
<223> OTHER INFORMATION: metallopeptide library member
<220> FEATURE:
<221> NAME/KEY: misc_feature
<222> LOCATION: (2)..(2)
<223> OTHER INFORMATION: Xaa is 2'-Naphthylalanine

<400> SEQUENCE: 9

His Xaa Cys Trp
1

<210> SEQ ID NO 10
<211> LENGTH: 4
<212> TYPE: PRT
<213> ORGANISM: artificial
<220> FEATURE:
<223> OTHER INFORMATION: metallopeptide sequence targeted for human
      neutrophil elastase

<400> SEQUENCE: 10

Leu Ser Cys Val
1

<210> SEQ ID NO 11
<211> LENGTH: 4
<212> TYPE: PRT
<213> ORGANISM: artificial
<220> FEATURE:
<223> OTHER INFORMATION: metallopeptide sequence targeted for human
      neutrophil elastase

<400> SEQUENCE: 11

Ile Ser Cys Val
1

<210> SEQ ID NO 12
<211> LENGTH: 5
<212> TYPE: PRT
<213> ORGANISM: artificial
<220> FEATURE:
<223> OTHER INFORMATION: two cysteine metallopeptide library member
<220> FEATURE:
<221> NAME/KEY: misc_feature
<222> LOCATION: (1)..(1)
<223> OTHER INFORMATION: Xaa is Tyr(But)
<220> FEATURE:
<221> NAME/KEY: misc_feature
<222> LOCATION: (2)..(2)
<223> OTHER INFORMATION: Xaa is Cys(Trt)
<220> FEATURE:
<221> NAME/KEY: misc_feature
<222> LOCATION: (3)..(3)
<223> OTHER INFORMATION: Xaa is an alpha amino acid
<220> FEATURE:
<221> NAME/KEY: misc_feature
<222> LOCATION: (5)..(5)
<223> OTHER INFORMATION: Xaa is Cys(StBu)

<400> SEQUENCE: 12

Xaa Xaa Xaa Phe Xaa
```

```
1               5

<210> SEQ ID NO 13
<211> LENGTH: 5
<212> TYPE: PRT
<213> ORGANISM: artificial
<220> FEATURE:
<223> OTHER INFORMATION: two cysteine metallopeptide library member
<220> FEATURE:
<221> NAME/KEY: misc_feature
<222> LOCATION: (1)..(1)
<223> OTHER INFORMATION: Xaa is Tyr(But)
<220> FEATURE:
<221> NAME/KEY: misc_feature
<222> LOCATION: (2)..(2)
<223> OTHER INFORMATION: Xaa is Cys(Trt)
<220> FEATURE:
<221> NAME/KEY: misc_feature
<222> LOCATION: (5)..(5)
<223> OTHER INFORMATION: Xaa is Cys(StBu)

<400> SEQUENCE: 13

Xaa Xaa Gly Phe Xaa
1               5
```